(12) United States Patent
Hwang et al.

(10) Patent No.: US 8,906,898 B1
(45) Date of Patent: Dec. 9, 2014

(54) SOLID FORMS OF CEFTOLOZANE

(71) Applicant: Calixa Therapeutics, Inc., Lexington, MA (US)

(72) Inventors: You Seok Hwang, Windham, NH (US); Nicole Miller Damour, Belmont, MA (US); Lisa Duong, Lynn, MA (US); Valdas Jurkauskas, Cambridge, MA (US); Kristos Adrian Moshos, Belmont, MA (US); Sanjay Mudur, Woburn, MA (US); Asli Ovat, Maynard, MA (US); Joseph Terracciano, Concord, MA (US); Jason Woertink, Sudbury, MA (US)

(73) Assignee: Calixa Therapeutics, Inc., Lexington, MA (US)

( * ) Notice: Subject to any disclaimer, the term of this patent is extended or adjusted under 35 U.S.C. 154(b) by 0 days.

(21) Appl. No.: 14/289,224

(22) Filed: May 28, 2014

Related U.S. Application Data

(60) Provisional application No. 61/883,530, filed on Sep. 27, 2013.

(51) Int. Cl.
*A01N 43/00* (2006.01)
*A61K 31/00* (2006.01)
*C07D 501/00* (2006.01)
*C07D 501/60* (2006.01)
*A61K 31/431* (2006.01)
*A61K 31/546* (2006.01)

(52) U.S. Cl.
CPC ............ *C07D 501/60* (2013.01); *A61K 31/431* (2013.01); *A61K 31/546* (2013.01)
USPC ..................................... 514/210.05; 540/217

(58) Field of Classification Search
USPC ..................................... 514/210.05; 540/217
See application file for complete search history.

(56) References Cited

U.S. PATENT DOCUMENTS

| | | | |
|---|---|---|---|
| 4,200,575 A | 4/1980 | Numata et al. |
| 4,246,405 A | 1/1981 | Takaya et al. |
| 4,255,431 A | 3/1981 | Junggren et al. |
| 4,264,597 A | 4/1981 | Hashimoto et al. |
| 4,267,176 A | 5/1981 | Kamiya et al. |
| 4,268,509 A | 5/1981 | Teraji et al. |
| 4,284,631 A | 8/1981 | Takaya et al. |
| 4,291,031 A | 9/1981 | Takaya et al. |
| 4,298,529 A | 11/1981 | Ueda et al. |
| 4,299,829 A | 11/1981 | Kamiya et al. |
| 4,305,937 A | 12/1981 | Kamiya et al. |
| 4,327,093 A | 4/1982 | Ueda et al. |
| 4,331,665 A | 5/1982 | Teraji et al. |
| 4,332,798 A | 6/1982 | Teraji et al. |
| 4,332,800 A | 6/1982 | Teraji et al. |
| 4,336,253 A | 6/1982 | Lunn |
| 4,338,313 A | 7/1982 | Teraji et al. |
| 4,339,449 A | 7/1982 | Hashimoto et al. |
| 4,363,807 A | 12/1982 | Takaya et al. |
| 4,367,228 A | 1/1983 | Takaya et al. |
| 4,368,325 A | 1/1983 | Ueda et al. |
| 4,369,312 A | 1/1983 | Hashimoto et al. |
| 4,370,326 A | 1/1983 | Takaya et al. |
| 4,381,299 A | 4/1983 | Teraji et al. |
| 4,390,534 A | 6/1983 | Teraji et al. |
| 4,394,384 A | 7/1983 | Takaya et al. |
| 4,402,955 A | 9/1983 | Lunn |
| 4,405,617 A | 9/1983 | Takaya et al. |
| 4,407,798 A | 10/1983 | Kamiya et al. |
| 4,409,214 A | 10/1983 | Takaya et al. |
| 4,409,215 A | 10/1983 | Takaya et al. |
| 4,409,217 A | 10/1983 | Takaya et al. |
| 4,416,879 A | 11/1983 | Takaya et al. |
| 4,418,058 A | 11/1983 | Hirai et al. |
| 4,420,477 A | 12/1983 | Takaya et al. |
| 4,423,213 A | 12/1983 | Takaya et al. |
| 4,425,340 A | 1/1984 | Teraji et al. |
| 4,425,341 A | 1/1984 | Takaya et al. |
| 4,427,677 A | 1/1984 | Takaya et al. |
| 4,430,499 A | 2/1984 | Wheeler |
| 4,431,642 A | 2/1984 | Teraji et al. |
| 4,436,912 A | 3/1984 | Wheeler |
| 4,438,113 A | 3/1984 | Takaya et al. |
| 4,443,443 A | 4/1984 | Ueda et al. |
| 4,443,444 A | 4/1984 | Takaya et al. |
| 4,447,429 A | 5/1984 | Teraji et al. |
| 4,450,270 A | 5/1984 | Lunn |
| 4,452,851 A | 6/1984 | Takaya et al. |
| 4,457,928 A | 7/1984 | Teraji et al. |
| 4,462,999 A | 7/1984 | Takaya et al. |

(Continued)

FOREIGN PATENT DOCUMENTS

| | | |
|---|---|---|
| AU | 614793 B1 | 5/1989 |
| AU | 707730 B2 | 5/1996 |

(Continued)

OTHER PUBLICATIONS

Bulik et al, In vivo comparison of CXA-101 with and without tazobactam versus piperacillin-tazobactam using human simulated exposures against phenotypically diverse gram-negative organisms. Antimicrob Agent Chemother 2012 56 (1):544-9.

Bulik et al., In vitro potency of CXA-101, a novel cephalosporin, against *Pseudomonas aeruginosa* displaying various resistance phenotypes, including multidrug resistance. Antimicrob Agents Chemother. 2010;54(1):557-9.

Chandorkar et al., Intrapulmonary penetration of ceftolozaneltazobactam and piperacillin/tazobactam in healthy adult subjects. J Antimicrob Chemother. 2012, 67, 2463.

Clinical and Laboratory Standards Institute CLSI Document M07-A9.

(Continued)

*Primary Examiner* — Sarah Pihonak

(74) *Attorney, Agent, or Firm* — Lathrop & Gage LLP; Brian C. Trinque

(57) ABSTRACT

Novel solid forms of ceftolozane are described, as well as methods for the preparation and use of these solid forms.

30 Claims, 5 Drawing Sheets

(56) References Cited

U.S. PATENT DOCUMENTS

| | | | |
|---|---|---|---|
| 4,463,000 A | 7/1984 | Teraji et al. |
| 4,463,002 A | 7/1984 | Takaya et al. |
| 4,463,003 A | 7/1984 | Takaya et al. |
| 4,464,369 A | 8/1984 | Takaya et al. |
| 4,470,980 A | 9/1984 | Higuchi et al. |
| 4,474,779 A | 10/1984 | Nagano et al. |
| 4,477,447 A | 10/1984 | Ueda et al. |
| 4,487,768 A | 12/1984 | Takaya et al. |
| 4,495,182 A | 1/1985 | Teraji et al. |
| 4,496,562 A | 1/1985 | Takaya et al. |
| 4,499,088 A | 2/1985 | Takaya et al. |
| 4,501,739 A | 2/1985 | Lunn et al. |
| 4,515,788 A | 5/1985 | Takaya et al. |
| 4,521,413 A | 6/1985 | Teraji et al. |
| 4,529,592 A | 7/1985 | Micetich et al. |
| 4,546,101 A | 10/1985 | Takaya et al. |
| 4,550,102 A | 10/1985 | Teraji et al. |
| 4,559,334 A | 12/1985 | Takaya et al. |
| 4,562,073 A | 12/1985 | Micetich et al. |
| 4,563,449 A | 1/1986 | Teraji et al. |
| 4,577,014 A | 3/1986 | Lunn et al. |
| 4,584,290 A | 4/1986 | Takaya et al. |
| 4,585,872 A | 4/1986 | Teraji et al. |
| 4,590,186 A | 5/1986 | Takaya et al. |
| 4,600,772 A | 7/1986 | O'Callaghan et al. |
| 4,608,373 A | 8/1986 | Shibanuma et al. |
| 4,609,730 A | 9/1986 | Takaya et al. |
| 4,616,083 A | 10/1986 | Shima et al. |
| 4,622,318 A | 11/1986 | Takaya et al. |
| 4,626,384 A | 12/1986 | Tanaka et al. |
| 4,631,274 A | 12/1986 | Takaya et al. |
| 4,640,915 A | 2/1987 | Hashimoto et al. |
| 4,647,556 A | 3/1987 | Lattrell et al. |
| 4,667,028 A | 5/1987 | Schwab et al. |
| 4,690,921 A | 9/1987 | Shibanuma et al. |
| 4,692,443 A | 9/1987 | Katner |
| 4,698,337 A | 10/1987 | Takaya et al. |
| 4,699,980 A | 10/1987 | Shibanuma et al. |
| 4,703,046 A | 10/1987 | Ueda et al. |
| 4,705,851 A | 11/1987 | Takaya et al. |
| 4,735,937 A | 4/1988 | Heusler et al. |
| 4,748,172 A | 5/1988 | Katner |
| 4,761,410 A | 8/1988 | Takaya et al. |
| 4,764,606 A | 8/1988 | Imai et al. |
| 4,769,183 A | 9/1988 | Kawamata et al. |
| 4,808,617 A | 2/1989 | Kaplan et al. |
| 4,808,711 A | 2/1989 | Shimizu et al. |
| 4,822,787 A | 4/1989 | Murata et al. |
| 4,833,134 A | 5/1989 | Kishimoto et al. |
| 4,861,769 A | 8/1989 | Takaya et al. |
| 4,868,174 A | 9/1989 | Takaya et al. |
| 4,871,730 A | 10/1989 | Takaya et al. |
| 4,882,434 A | 11/1989 | Yoshioka |
| 4,921,852 A | 5/1990 | Murata et al. |
| 4,923,857 A | 5/1990 | Murata et al. |
| 4,925,934 A | 5/1990 | Taniguchi et al. |
| 4,927,818 A | 5/1990 | Takaya et al. |
| 4,935,507 A | 6/1990 | Takaya et al. |
| 4,943,567 A | 7/1990 | Nishizawa et al. |
| 4,952,578 A | 8/1990 | Sakane et al. |
| 4,960,766 A | 10/1990 | Takaya et al. |
| 4,963,543 A | 10/1990 | Murata et al. |
| 4,963,544 A | 10/1990 | Murata et al. |
| 4,971,962 A | 11/1990 | Oh et al. |
| 4,982,596 A | 1/1991 | Peterson et al. |
| 5,036,064 A | 7/1991 | Gotschi |
| RE33,778 E | 12/1991 | Iwanami et al. |
| 5,071,979 A | 12/1991 | Lattrell et al. |
| 5,073,550 A | 12/1991 | Gotschi |
| 5,081,116 A | 1/1992 | Nagano et al. |
| 5,095,012 A | 3/1992 | Okita et al. |
| 5,102,877 A | 4/1992 | Murata et al. |
| 5,104,866 A | 4/1992 | Sakane et al. |
| 5,108,997 A | 4/1992 | Takaya et al. |
| 5,109,130 A | 4/1992 | Sakane et al. |
| 5,138,066 A | 8/1992 | Gotschi |
| 5,159,070 A | 10/1992 | Heymes et al. |
| 5,162,520 A | 11/1992 | Takaya et al. |
| 5,173,485 A | 12/1992 | Sakane et al. |
| 5,179,485 A | 1/1993 | Tamayama |
| 5,187,160 A | 2/1993 | Sakane et al. |
| 5,194,432 A | 3/1993 | Takaya et al. |
| 5,210,080 A | 5/1993 | Takaya et al. |
| 5,215,982 A | 6/1993 | Sakane et al. |
| 5,215,983 A | 6/1993 | Murata et al. |
| 5,219,848 A | 6/1993 | Hennequin et al. |
| 5,234,920 A | 8/1993 | Okita et al. |
| 5,244,890 A | 9/1993 | Yamanaka et al. |
| 5,281,589 A | 1/1994 | Kim et al. |
| 5,286,721 A | 2/1994 | Murata et al. |
| 5,319,140 A | 6/1994 | Gotschi |
| 5,329,002 A | 7/1994 | Albrecht et al. |
| 5,336,768 A | 8/1994 | Albrecht et al. |
| 5,366,970 A | 11/1994 | Sakane et al. |
| 5,389,627 A | 2/1995 | Kim et al. |
| 5,498,787 A | 3/1996 | Wang et al. |
| 5,523,400 A | 6/1996 | Wei et al. |
| 5,637,580 A | 6/1997 | White et al. |
| 5,646,139 A | 7/1997 | White et al. |
| 5,648,346 A | 7/1997 | White et al. |
| 5,656,623 A | 8/1997 | White et al. |
| 5,661,144 A | 8/1997 | Tsushima et al. |
| 5,663,163 A | 9/1997 | Takaya et al. |
| 5,763,603 A | 6/1998 | Trickes |
| 6,207,661 B1 | 3/2001 | Thompson et al. |
| 6,214,818 B1 | 4/2001 | Nishitani et al. |
| 6,458,950 B1 | 10/2002 | Nishitani et al. |
| 6,518,263 B1 | 2/2003 | Nishitani et al. |
| 6,660,855 B2 | 12/2003 | Shimabayashi et al. |
| 6,774,104 B1 | 8/2004 | Sawai et al. |
| 6,800,621 B2 | 10/2004 | Nishitani et al. |
| 6,878,686 B2 | 4/2005 | Marquess et al. |
| 6,936,711 B2 | 8/2005 | Deshpande et al. |
| 6,974,797 B2 | 12/2005 | Fatheree et al. |
| 6,995,138 B2 | 2/2006 | Marquess et al. |
| 7,067,481 B2 | 6/2006 | Fatheree et al. |
| 7,067,482 B2 | 6/2006 | Fatheree et al. |
| 7,112,565 B2 | 9/2006 | Sawai et al. |
| 7,129,232 B2 | 10/2006 | Ohki et al. |
| 7,179,801 B2 | 2/2007 | Ohki et al. |
| 7,192,943 B2 | 3/2007 | Yamanaka et al. |
| 7,273,935 B2 | 9/2007 | Deshpande et al. |
| 7,279,458 B2 | 10/2007 | Fatheree et al. |
| 7,304,075 B2 | 12/2007 | Araki et al. |
| 7,332,471 B2 | 2/2008 | Fatheree et al. |
| 7,341,993 B2 | 3/2008 | Fatheree et al. |
| 7,384,928 B2 | 6/2008 | Nishitani et al. |
| 7,417,143 B2 | 8/2008 | Gnanaprakasam et al. |
| 7,547,777 B2 | 6/2009 | Tokumaru et al. |
| 7,553,962 B2 | 6/2009 | Fatheree et al. |
| 7,601,690 B2 | 10/2009 | Fatheree et al. |
| 7,612,037 B2 | 11/2009 | Fatheree et al. |
| 7,649,080 B2 | 1/2010 | Fatheree et al. |
| 7,655,621 B2 | 2/2010 | Fatheree et al. |
| 7,674,898 B2 | 3/2010 | Shimabayashi et al. |
| 7,728,127 B2 | 6/2010 | Fatheree et al. |
| 7,842,683 B2 | 11/2010 | Koppel |
| 7,915,229 B2 | 3/2011 | Cohen et al. |
| 8,133,883 B2 | 3/2012 | Cohen et al. |
| 8,476,425 B1 | 7/2013 | Lai et al. |
| 2002/0115650 A1 | 8/2002 | Glinka |
| 2002/0193587 A1 | 12/2002 | Shimabayashi et al. |
| 2003/0130173 A1 | 7/2003 | Fatheree et al. |
| 2003/0232983 A1 | 12/2003 | Deshpande et al. |
| 2004/0248875 A1 | 12/2004 | Ohki et al. |
| 2005/0004094 A1 | 1/2005 | Yamanaka et al. |
| 2005/0096306 A1 | 5/2005 | Yamanaka et al. |
| 2005/0171077 A1 | 8/2005 | Ruppen et al. |
| 2005/0228176 A1 | 10/2005 | Gnanaprakasam et al. |
| 2006/0051412 A1 | 3/2006 | Petereit et al. |
| 2006/0084639 A1 | 4/2006 | Cohen et al. |
| 2006/0099253 A1 | 5/2006 | Becker et al. |
| 2006/0173177 A1 | 8/2006 | Gego et al. |
| 2006/0241017 A1 | 10/2006 | Chandran |

(56) References Cited

U.S. PATENT DOCUMENTS

| | | |
|---|---|---|
| 2006/0269485 A1 | 11/2006 | Friedman et al. |
| 2006/0287244 A1 | 12/2006 | Chandran |
| 2006/0293516 A1 | 12/2006 | Wada et al. |
| 2007/0054899 A1 | 3/2007 | Park et al. |
| 2007/0116770 A1 | 5/2007 | Garms et al. |
| 2007/0219191 A1 | 9/2007 | Nishitani et al. |
| 2007/0286817 A1 | 12/2007 | Tatapudy et al. |
| 2007/0286818 A1 | 12/2007 | Tatapudy et al. |
| 2008/0015156 A1 | 1/2008 | Udayampalayam Palanisamy et al. |
| 2008/0160067 A1 | 7/2008 | Boeckh et al. |
| 2008/0233196 A1 | 9/2008 | Cattaneo et al. |
| 2009/0098088 A1 | 4/2009 | Taylor et al. |
| 2009/0137460 A1 | 5/2009 | Marquess et al. |
| 2009/0155387 A1 | 6/2009 | Zhang |
| 2009/0156517 A1 | 6/2009 | Zhang |
| 2009/0156518 A1 | 6/2009 | Zhang |
| 2009/0186865 A1 | 7/2009 | Diago et al. |
| 2009/0227554 A1 | 9/2009 | Liversidge et al. |
| 2009/0274662 A1 | 11/2009 | Magowan et al. |
| 2009/0275552 A1 | 11/2009 | Patel et al. |
| 2009/0291102 A1 | 11/2009 | Fortin |
| 2009/0311234 A1 | 12/2009 | Koski et al. |
| 2010/0040548 A1 | 2/2010 | Yu |
| 2010/0286031 A1 | 11/2010 | Charan et al. |
| 2011/0044917 A1 | 2/2011 | Tosetti |
| 2011/0136763 A1 | 6/2011 | Xia et al. |
| 2011/0190252 A1 | 8/2011 | Watson et al. |
| 2011/0257079 A1 | 10/2011 | Chaudhary et al. |
| 2013/0065874 A1 | 3/2013 | Chandorkar et al. |

FOREIGN PATENT DOCUMENTS

| | | |
|---|---|---|
| AU | 2002952355 | 10/2002 |
| AU | 2003904813 | 9/2003 |
| AU | 2003905084 | 9/2003 |
| CA | 1235689 A1 | 4/1988 |
| CA | 2140701 A1 | 7/1995 |
| CN | 99100092 | 12/1999 |
| CN | 200410067367 | 4/2006 |
| CN | 200810092568 | 10/2008 |
| CN | 200810238479 | 5/2009 |
| CN | 200910169647 | 4/2010 |
| CN | 201010557481 | 4/2011 |
| CN | 201110061045 | 3/2012 |
| EP | 0047977 A1 | 9/1981 |
| EP | 0097446 A1 | 1/1984 |
| EP | 0137440 | 4/1985 |
| EP | 0137442 A2 | 4/1985 |
| EP | 0138552 | 4/1985 |
| EP | 0111934 B1 | 8/1988 |
| EP | 0318767 A2 | 6/1989 |
| EP | 0664117 A1 | 7/1995 |
| EP | 0711774 B1 | 5/1996 |
| EP | 0771803 A1 | 5/1997 |
| EP | 1273586 A1 | 1/2003 |
| EP | 1285923 A1 | 2/2003 |
| EP | 1468697 A1 | 10/2004 |
| EP | 1134222 B1 | 4/2005 |
| EP | 1554287 | 7/2005 |
| EP | 1671974 A1 | 6/2006 |
| EP | 1686131 A2 | 8/2006 |
| EP | 1759697 A1 | 3/2007 |
| EP | 1787641 A1 | 5/2007 |
| EP | 1959933 | 8/2008 |
| EP | 1974721 A1 | 10/2008 |
| EP | 2015755 | 1/2009 |
| EP | 2062581 A1 | 5/2009 |
| EP | 2062582 A1 | 5/2009 |
| EP | 2062585 A1 | 5/2009 |
| EP | 2136844 | 12/2009 |
| EP | 2305251 A2 | 4/2011 |
| EP | 1154770 | 11/2011 |
| JP | 62103092 A | 5/1987 |
| JP | 62158290 A | 7/1987 |
| JP | 63051388 A | 3/1988 |
| JP | 63051389 A | 3/1988 |
| JP | 2088582 A | 3/1990 |
| JP | 2117678 A | 5/1990 |
| JP | 4288086 A | 10/1992 |
| JP | 5222058 A | 8/1993 |
| JP | 6056848 A | 3/1994 |
| JP | 6128268 A | 5/1994 |
| JP | 2005162670 A | 6/2005 |
| WO | 9512601 A1 | 5/1995 |
| WO | 9741128 A1 | 11/1997 |
| WO | WO 99/28308 | 6/1999 |
| WO | WO 99/64049 | 12/1999 |
| WO | WO0004915 A1 | 2/2000 |
| WO | 0050035 A2 | 8/2000 |
| WO | 02090363 A1 | 11/2002 |
| WO | 02090364 A1 | 11/2002 |
| WO | 02092605 A1 | 11/2002 |
| WO | 02102378 A1 | 12/2002 |
| WO | 03066053 A1 | 8/2003 |
| WO | WO 03/078440 | 9/2003 |
| WO | 03104241 A1 | 12/2003 |
| WO | 2004019901 A1 | 3/2004 |
| WO | 2004039776 A2 | 5/2004 |
| WO | WO 2004/048551 | 6/2004 |
| WO | 2004066976 A1 | 8/2004 |
| WO | 2004098643 A1 | 11/2004 |
| WO | WO 2005/005436 | 1/2005 |
| WO | 2005074925 A1 | 8/2005 |
| WO | 2006044600 A1 | 4/2006 |
| WO | 2006045006 A1 | 4/2006 |
| WO | 2006088305 A1 | 8/2006 |
| WO | 2007065862 A1 | 6/2007 |
| WO | 2007086011 A1 | 8/2007 |
| WO | 2007086013 A1 | 8/2007 |
| WO | 2007086014 A1 | 8/2007 |
| WO | 2007099396 A2 | 9/2007 |
| WO | 2007129176 A2 | 11/2007 |
| WO | 2007145866 A1 | 12/2007 |
| WO | 2007145868 A1 | 12/2007 |
| WO | 2008030469 A2 | 3/2008 |
| WO | 2008065247 A1 | 6/2008 |
| WO | 2008075207 A2 | 6/2008 |
| WO | 2008101743 A2 | 8/2008 |
| WO | 2008113177 A1 | 9/2008 |
| WO | 2009048603 A1 | 4/2009 |
| WO | WO 2009/105782 | 8/2009 |
| WO | 2009122252 A2 | 10/2009 |
| WO | 2009134948 A1 | 11/2009 |
| WO | 2010014285 A1 | 2/2010 |
| WO | 2010142241 A1 | 12/2010 |
| WO | 2011101710 A1 | 8/2011 |
| WO | 2011112435 A1 | 9/2011 |
| WO | 2011127200 A2 | 10/2011 |
| WO | WO2013036783 A2 | 3/2013 |

OTHER PUBLICATIONS

Clinical and Laboratory Standards Institute CLSI Document M100-S22.

Ge et al., Pharmacokinetics and safety of CXA-101, a new antipseudomonal cephalosporin, in healthy adult male and female subjects receiving single- and multiple-dose intravenous infusions. Antimicrob Agents Chemother. 2010 , 54: 3427-31.

Juan et al., Activity of a new antipseudomonal cephalosporin, CXA-101, against carbapenem-resistant and multidrug-resistant *Pseudomonas aeruginosa* clinical strains. Antimicrob Agents Chemother. 2010;54(2):846-51.

Livermore et al., Chequerboard titration of cephalosporin CXA-101 and tazobactam versus beta-lactamase-producing Enterobacteriaceae. J Antimicrob Chemother. 2010 65 1972-4.

Miller et al., Pharmacokinetics and Safety of Intravenous Ceftolozane/tazobactam in Healthy Adult Subjects following Single and Multiple Ascending Doses. Antimicrob Agents Chemother. 2012 56:3086-91.

(56) References Cited

OTHER PUBLICATIONS

Moya et al., Activity of a new cephalosporin, CXA-101 (FR264205), against beta-lactam-resistant *Pseudomonas aeruginosa* mutants selected in vitro and after antipseudomonal treatment of intensive care unit patients. Antimicrob Agents Chemother. 2010 ;54(3):1213-7.

Moya et al., Affinity of the New Cephalosporin CXA-101 to Penicillin-Binding Proteins of *Pseudomonas aeruginosa*. Antimicrob Agents Chemother. 2010; 54: 3933-3937.

Moya et al., Pan-Beta-Lactam Resistance Development in *Pseudomonas aeruginosa* Clinical Strains: Molecular Mechanisms, Penicillin-Binding Protein Profiles, and Binding Affinities. Antimicrob Agents Chemother. 2012 56 4771-8.

Perletti et al., CXA-101—Cephalosporin Antibiotic. Drugs of the Future 2010; 35(12): 977-986.

Riera et al., Anti-biofilm and resistance suppression activities of CXA-101 against chronic respiratory infection phenotypes of *Pseudomonas aeruginosa* strain PAO1. J Antimicrob Chemother. 2010;65(7):1399-1404.

Sader et al., Antimicrobial activity of CXA-101, a novel cephalosporin tested in combination with tazobactam against Enterobacteriaceae, *Pseudomonas aeruginosa*, and *Bacteroides fragilis* strains having various resistance phenotypes. Agents Chemother. 2011 55(5):2390-4.

Zamorano et al., Activity of the new cephalosporin CXA-101 against *Pseudomonas aeruginosa* isolates from chronically-infected cystic fibrosis patients. Clin Microbiol Infect. 2010 16(9):1482-7.

Alexov et al. Efficacy of Ampicillin-Sulbactam is not Dependent upon Maintenance of a Critical Ratio between Components: Sulbactam Pharmacokinetics in Pharmacodynamic Interactions. Antimcirobial Agents Chemotherapy 1996;40:2468.

Bush et al. Kinetic Interactions of Tazobactam with Beta-Lactamases from All Major Structural Classes. Antimicrobial Agents and Chemotherapy 1993;37:851.

Hatano et al. In vivo Anti-*Pseudomonas aeruginosa* Activity of Novel Parenteral Cephalosporin, FR264205. 45th Annual Interscience Conference on Antimicrobial Agents and Chemotherapy (ICAAC 2005); Dec. 16-19, 2005. Oral Presentation F-1165.

Kurpiel. Point Mutations in the Inc Antisense RNA Gene are Associated with Increased Plasmid Copy Number, Expression of BlaCMY-2 and Resistance to Piperacillin/Tazobactam in *Escherichia coli*. Journal of Antimicrobial Chemotherapy 2012;67:339.

Lister et al. Importance of Beta-Lactamase Inhibitor Pharmacokinetics in the Pharmacodynamics of Inhibitor-Drug Combinations: Studies with Piperacillin-Tazobactam and Piperacillin-sulbactam. Antimicrobial Agents and Chemotherapy 1997;41:721.

Louie et al., Pharmacodynamics of b-Lactamase Inhibition by NXL104 in Combination with Cefaroline: Examining Organisms with Multiple Types of b-Lacramases. Antimicrobial Agents and Chemotherapy. 2012, 56, 258.

Miller et al. CXA-201 dose selection based on probability of target attainment and drug exposure in subjects with varying degrees of renal impairment. ICAAC 2011. Oral Presentation A-1099.

Seetulsingh et al. Activity of Clavulanate Combinations against TEM-1 b-Lactamase-Producing *Escherichia coli* Isolates Obtained in 1982 and 1989. Journal of Antimicrobial Chemotherapy 1991;27:749.

Soon et al. A Novel Mathematical Modeling Approach to Characterize the Pharmacodynamics of Ceftolozane/Tazobactam, a β-lactam & β-lactannase Inhibitor Combination. 52nd Annual Interscience Conference on Antimicrobial and Chemotherapy (ICAAC 2012); Sep. 9-12, 2012. Oral Presentation A-1762.

Steenbergen et al. Potency of CXA-101Tazobactam for Pathogens from ICU and non-ICU Correlated to Probability of Pharmacokinetic/Pharmacodynamic (PK/PD) Target Attainment. ICAAC 2011. Oral Presentation A-1689.

Strayer et al. Pharmacodynamics of Piperacillin Alone and in Combination with Tazobactam against Piperacillin-Resistant and -Susceptible Organisms in an in Vitro Model of Infection. Antimicrobial Agents and Chemotherapy 1994;38:2351.

Thomson et al. Beta-Lactamase Production in Memebers of the Family Enterobacteriaceae and Resistance to Beta-Lactam-Enzyme Inhibitor Combinations. Antimicrobial Agents and Chemotherapy 1990;34:622.

Abstract for Brown et al. Activity profile of CXA-101 against gram-positive and gram-negative pathogens by broth and agar dilution. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-354; This poster is obtainable at: http://www.eurofins.com/media/694466/Calixe/020F1-354%20broth%20agar%20v6.pdf.

Abstract for Brown et al. Activity profile of CXA-101 and CXA-101/tazobactam against target gram-positive and gram-negative pathogens. 49th Annual Interscience Conference on Antimicrobial Agents and Chemotherapy (ICAAC 2009); 12th-15th, 2009. Poster F1-1986; This poster is obtainable at: http://www.eurofins.com/media/767069/Final%20F1-1986.pdf.

Abstract for Brown et al. Effect of various testing parameters on the activity of CXA-101 by broth microdilution. 48th Annual Interscience Conference on Antimicrobial Agents and Chemotherapy & the Infectious Disease Society of America 46th Annual Meeting (ICAAC/IDSA 2008); Oct 25-28, 2008. Poster F1-357; This poster is obtainable at: http://www.eurofins.com/media/694469/CW/020F1-357%20parameter%20v6.pdf.

Abstract for Brown et al. Mode of action of CXA-101 based on minimum bactericidal concentration analysis and time-kill kinetic analysis. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-358; This poster is obtainable at: http://www.eurofins.com/media/694472/CXA%20F1-358°/020tV/020mbe/020v5.pdf.

Abstract for Brown et al., Disk diffusion testing of CXA-101 and CXA-101 in combination with tazobactam against target pathogens. 49th Annual Interscience Conference on Antimicrobial Agents and Chemotherapy (ICAAC 2009); 12th-15th, 2009. Poster F1-1998; This poster is obtainable at: http:/lwww.eurofins.com/media/767072/Final%20F1-1998.pdf.

Abstract for Brown et al., Quality control parameters for CXA-101 broth microdilution susceptibility tests. 49th Annual Interscience Conference on Antimicrobial Agents and Chemotherapy (ICAAC 2009); Sep. 12-15, 2009. Poster F1-1997.

Abstract for Bulik et al. In vivo Comparison of CXA-101 (FR264205) with and without Tazobactam verus Piperacillin-Tazobactam Using Human Simulated Exposures against Phenotypically Diverse Gram-Negative Organisms. ICAAC 2010. Poster A1-1381; This poster is obtainable at: http://www.cubist.com/downloads/Bulik_PP_ICAAC_2010_in_vivo_CXA-101_vs_TZP_against_gram_neg.pdf.

Abstract for Cabot et al. Activity of CXA-101 Against a Large Collection of *P. aeruginosa* Blood Stream Isolates Overexpressing AmpC and the Major Efflux Pumps. 50th Annual Interscience Conference on Antimicrobial Agents and Chemotherapy (ICAAC 2010); Sep. 12-15, 2010. Poster E-816.

Abstract for Chandorkar et al. Penetration of Ceftolozane/Tazobactam and Piperacillin/Tazobactam into the Epithelial lining of Fluid of Healthy Volunteers. 22nd Annual Meeting of the European Congress of Clinical Microbiology (ECCMID 2012); Mar. 31-Apr. 3, 2012. Poster P1627.

Abstract for Chandorkar et al. Intrapulmonary penetration of CXA-201 and Piperacillin/tazobactam in healthy adult subjects. 49th Annual Meeting of the Infectious Diseases Society of America (IDSA 2011); Oct. 20-23, 2011. Poster 611.

Abstract for Craig et al., In vivo activity of CXA-101 plus a 2:1, 4:1, or 8:1 ratio of tazobactam against various Enterobacteriaceae producing Extended-spectrum beta-lactamases in the thighs of neutropenic mice. 49th Annual Interscience Conference on Antimicrobial Agents and Chemotherapy (ICAAC 2009); Sep. 12-15, 2009. Poster F1-1999.

Abstract for Craig et al., In vivo activity of CXA-101, a new cephalosporin, against *Pseudomonas aeruginosa* and other

(56) References Cited

OTHER PUBLICATIONS

Enterobacteriaceae in the thighs of neutropenic mice. 49th Annual Interscience Conference on Antimicrobial Agents and Chemotherapy (ICAAC 2009); Sep. 12-15, 2009. Poster F1-2002.

Abstract for Fenneteau et al. Population PK/PD Modeling and Simulations of a Fixed-Dose Combination of CXA-101 and Tazobactam to Optimize Dosing Strategies in Renally Impaired Patients with Complicated Urinary Tract Infection. 3rd Biennial American Conference on Pharmacometrics (ACoP 2011); Apr. 3-6, 2011; This poster is obtainable at: http://www.go-acop.org/sites/default/files/webform/posters/ACOP2011%20-%20Dosing%20Strategies%20of%20CXA-101%20and%20Taz%20in%20cUTI%20Patients.pdf.

Abstract for Ge et al., CXA-101 population PK analysis and Monte Carlo simulation for PK/PD target attainment and dose regimen selection. 49th Annual Interscience Conference on Antimicrobial Agents and Chemotherapy (ICAAC 2009); Sep. 12-15, 2009. Poster F1-2003.

Abstract for Ge et al., PK and safety of CXA-101, a new antipseudomonal cephalosporin, in healthy adult subjects after single intravenous dosing. 49th Annual Interscience Conference on Antimicrobial Agents and Chemotherapy (ICAAC 2009); Sep. 12-15, 2009. Poster F1-2004.

Abstract for Ge et al., PK study of CXA-101 in combination with tazobactam in dogs after intravenous administration. 49th Annual Interscience Conference on Antimicrobial Agents and Chemotherapy (ICAAC 2009); Sep. 12-15, 2009. Poster F1-2001.

Abstract for Giske et al., CXA-101 has high activity against clinical isolates of *Pseudomonas aeruginosa* including ceftazidime-resistant isolates. 49th Annual Interscience Conference on Antimicrobial Agents and Chemotherapy (ICAAC 2009); Sep. 12-15, 2009. Poster F1-1988.

Abstract for Hershberger et al. CXA-101 Tazobactam Probability of Target Attainment Using Population Pharmacokinetic Analysis. Joint Meeting of the European Congress of Clinical Microbiology and Infectious Diseases and International Congress of Chemotherapy (ECCMID-ICC 2011); May 7-12, 2011. Poster 1520; This poster is obtainable at: http://www.poster-submission.com/search/sresult.

Abstract for Jacqueline. Assessment of the in vivo Activity of CXA-101 in a Murine Model of *Pseudomonas aeruginosa* Pneumonia: Comparison with Ceftazidime and Piperacillin-Tazobactam. 50th Annual Interscience Conference on Antimicrobial Agents and Chemotherapy (ICAAC 2010); Sep. 12-15, 2010. Poster B-1401.

Abstract for Jacqueline et al. 50% effective dose determination of CXA-101 alone or in combination with tazobactam for treating experimental peritonitis in mice due to extended-spectrum beta-lactamase-producing *Escherichia coli* strains: comparison with ceftazidime and piperacillin/tazobactam. 49th Annual Interscience Conference on Antimicrobial Agents and Chemotherapy (ICAAC 2009); Sep. 12-15, 2009. Poster F1-2000.

Abstract for Jacqueline et al. FIC Index determination of CXA-101/tazobactam in combination with amikacin, aztreonam, meropenem, levofloxacin, and tigecycline against *Escherichia coli, Klebsiella pneumoniae*, and *Pseudomonas aeruginosa* strains. 49th Annual Interscience Conference on Antimicrobial Agents and Chemotherapy (ICAAC 2009); Sep. 12-15, 2009. Poster F1-1995.

Abstract for Jacqueline et al. In vitro assessment using time-kill curves of CXA-101/tazobactam against *Escherichia coli, Klebsiella pneumoniae*, and *Pseudomonas aeruginosa* strains. 49th Annual Interscience Conference on Antimicrobial Agents and Chemotherapy (ICAAC 2009); Sep. 12-15, 2009. Poster F1-1996.

Abstract for Juan et al., Oliver A. Activity of the new cephalosporin CXA-101 against carbapenem-resistant *Pseudomonas aeruginosa* isolates from a Spanish multicenter study. 49th Annual Interscience Conference on Antimicrobial Agents and Chemotherapy (ICAAC 2009); Sep. 12-15, 2009. Poster F1-1987.

Abstract for Killian et al. An Equivalency Study of a Sensititre Dried MIC Plate Compared with the CLSI Broth Microdilution Reference Method for CXA-201 and Comparator Antimicrobials. 51st Annual Interscience Conference on Antimicrobial Agents and Chemotherapy (ICAAC 2011); Sep. 17-20, 2011. Poster D-691A.

Abstract for Livermore et al., Warner M. Activity of cephalosporin CXA-101 vs. *P. aeruginosa*. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-355; This poster is obtainable at: http://www.hpa.org.uk/webc/HPAwebFile/HPAweb_C/1225354148015.

Abstract for Marier et al. Pharmacokinetics of a novel antipseudomonal cephalosporin, CXA-101, and tazobactam in healthy adult subjects. 50th Annual Interscience Conference on Antimicrobial Agents and Chemotherapy (ICAAC 2010); Sep. 12-15, 2010. Poster A1-1391.

Abstract for Marier et al. Population PK Analysis of Intravenous CXA-101 in Subjects with Complicated Urinary Tract Infection, Including Pyelonephritis. 112th Annual Meeting of the American Society for Clinical Pharmacology and Therapeutics (ASCPT 2011); Mar. 2-5, 2011. Poster PII-49.

Abstract for Hershberger et al. Pharmacokinetics of CXA-101/tazobactam in Subjects with Mild or Moderate Renal Impairment. Joint Meeting of the European Congress of Clinical Microbiology and Infectious Diseases and International Congress of Chemotherapy (ECCMID-ICC 2011); May 7-12, 2011. Poster 1519; This poster is obtainable at: http://www.poster-submission.com.

Abstract for Miller et al. Probability of Target Attainment of CXA-201 in Patients with Renal Hyperclearance. 49th Annual Meeting of the Infectious Diseases Society of America (IDSA 2011); Oct. 20-23, 2011. Poster B1-589.

Abstract for Miller et al., Safety and Pharmacokinetics of Intravenous Ceftolozane/tazobactam 3 g every 8 Hours and Cumulative Fraction of Response in Plasma and Epithelial Lining Fluid in a Simulated Ventilator Associated Pneumonia Population. 52nd Annual Interscience Conference on Antimicrobia Agents and Chemotherapy (ICAAC 2012); Sep. 9-12, 2012. Poster A-641.

Abstract for Moulds et al., Impact of characterized resistance mechanisms on the susceptibility of *Pseudomonas aeruginosa* to CXA-101. 50th Annual Interscience Conference on Antimicrobial Agents and Chemotherapy (ICAAC Sep. 12-15, 2010. Poster C1-1415; This poster is obtainable at: http://www.cubist.com/downloads/Moulds.PP.ICAAC_2010.Impact_of_resis_mech_on_suscep_of_P_aeruginosa_to_CXA_JNS.pdf.

Abstract for Moya et al. Affinity of the new cephalosporin CXA-101 to penicillin-binding proteins of *Pseudomonas aeruginosa*. 49th Annual Interscience Conference on Antimicrobial Agents and Chemotherapy (ICAAC 2009); Sep. 12-15, 2009. Poster F1-1985.

Abstract for Moya et al. Pan-Beta-lactam resistance development in *P. aeruginosa* clinical strains: molecular mechanisms, PBPs profiles and binding affinities. 51st Annual Interscience Conference on Antimicrobial Agents and Chemotherapy (ICAAC 2011); Sep. 17-20, 2011. Poster C1-619.

Abstract for Mushtaq et al. Activity of cephalosporin CXA-101 with B-lactamase inhibitors vs. Enterobacteriaceae. 48th Annual Interscience Conference on Antimicrobial Agents and Chemotherapy & the Infectious Disease Society of America 46th Annual Meeting (ICAAC/IDSA 2008); Oct. 25-28, 2008. Poster F1-356; This poster is obtainable at: http://www.hpa.org.uk/webc/HPAwebFile/HPAweb_C/1225354148047.

Abstract for Riera et al. Activity of the new cephalosporin CXA-101 against biofilms of relevant *P. aeruginosa* phenotypes in cystic fibrosis chronic respiratory infection: mucoid and hypermutable strains. 49th Annual Interscience Conference on Antimicrobial Agents and Chemotherapy (ICAAC 2009); Sep. 12-15, 2009. Poster F1-1990.

Abstract for Sader et al., Activity of the Novel Antimicrobial Ceftolozane)Tazobactam Tested Against Bacterial Isolates in USA Hospitals from Patients with Pneumonia (2011). IDWeek 2012: A Joint Meeting of IDSA, SHEA, HIVA, and PIDS; Oct. 17-21, 2012. Poster 846; This poster is obtainable at: http://www.jmilabs.com/data/posters/IDWeek2012/846.Pdf.

Abstract for Sader et al., Activity of the Novel Antimicrobial Ceftolozane)Tazobactam Tested Against Contemporary Clinical Strains from USA Hospitals (2011). 52nd Annual Interscience Conference on Antimicrobial Agents and Chemotherapy (ICAAC 2012); Sep. 9-12, 2012. Poster E-199.

(56) References Cited

OTHER PUBLICATIONS

Abstract for Sader et al., Activity of the Novel Antimicrobial CXA-201 Tested Against Contemporary Clinical Strains from European Hospitals. 22nd Annual Meeting of the European Congress of Clinical Microbiology (ECCMID 2012); Mar. 31-Apr. 3, 2012. Poster P1446.

Abstract for Sader et al., Activity of the novel cephalosporin CXA-101 tested in combination with tazobactam against cephalosporin-resistant Enterobacteriaceae, *P. aeruginosa* and *B. fragilis*. 49th Annual Interscience Conference on Antimicrobial Agents and Chemotherapy (ICAAC 2009); Sep. 12-15, 2009. Poster F1-1992; This poster is obtainable at: http://www.jmilabs.com/data/posters/ICAAC2009/F1-1992.pdf.

Abstract for Snydman et al., Activity of Ceftolozane/Tazobactam CXA-201 against 270 recent isolates from the bacteroides group. 22nd Annual Meeting of the European Congress of Clinical Microbiology (ECCMID 2012); Mar. 31-Apr. 3, 2012. Poster; This poster is obtainable at: http://www.escmid_orgtescmid_library/online_lecture_library/?search=l&current_page=l&search_term=snydman.

Abstract for Soon et al., In vitro Pharmacodynamics of CXA-201 (Ceftolozane/Tazobactam) against Beta-lactamase Producing *Eschericia coli*. 52nd Annual Interscience Conference on Antimicrobial Agents and Chemotherapy (ICAAC 2012); Sep. 9-12, 2012. Poster E-201.

Abstract for Titelman et al. Activity of CXA-101 plus tazobactam against ESBL-producing *E. coli* and *K. pneumoniae*. 49th Annual Interscience Conference on Antimicrobial Agents and Chemotherapy (ICAAC 2009); Sep. 12-15, 2009. Poster F1-1993.

Abstract for Umeh et al., A double-blind, randomized, phase 2 study to compare the safety and efficacy of intravenous CXA-101 and intravenous ceftazidime in complicated urinary tract infection. 50th Annual Interscience Conference on Agents and Chemotherapy (ICAAC 2010); Sep. 12-15, 2010. Poster L1-361A; This poster is obtainable at: http://www.cubist.com/downloads/Umeh_ICAAC2010_08144v2.pdf.

Abstract for Walkty et al. In Vitro Activity of Ceftolozane/Tazobactam (CXA-201) versus *Pseudomonas aeruginosa* Isolates Obtained from Patients in Canadian Hospitals: CANWARD 2011. IDWeek 2012: A Joint Meeting of IDSA, SHEA, HIVMA, and PIDS; Oct. 17-21, 2012. Poster 1616; This poster is obtainable at: https://idsa.confex.com/idsa/2012/webprogram/Handouttid509/POSTER202_1616.pdf.

Abstract for Zamorano et al. Activity of the new cephalosporin CXA-101 against *P. aeruginosa* isolates from chronically infected cystic fibrosis patients. 49th Annual Interscience Conference on Antimicrobial Agents and Chemotherapy (ICAAC 2009); Sep. 12-15, 2009. Poster F1-1991.

Abstract for Zhanel et al., In vitro Activity of Ceftolozane/tazobactam Tested Against 1,705 Gram-Negative Pathogens Isolated from Patients in Canadian Hospitals in 2011: CANWARD Surveillance Study. 52nd Annual Interscience Conference on Antimicrobial Agents and Chemotherapy (ICAAC 2012); Sep. 9-12, 2012. Poster E-200.

Wooley et al. 'Impact of renal function on the pharmacokinetics and safety of ceftolozane-tazobactam'. Antimicrob Agents Chemother. 2014 vol. 58, No. 4, pp. 2249-2255.

Sader et al. 'Post-β-Lactamase-Inhibitor Effect of Tazobactam in Combination with Ceftolozane on Extended-Spectrum-β-Lactamase-Producing Strains'. Antimicrob Agents Chemother. 2014 vol. 58 No. 4, pp. 2434-243.

Cabot et al. '*Pseudomonas aeruginosa* Ceftolozane-Tazobactam Resistance Development Requires Multiple Mutations Leading to Overexpression and Structural Modification of AmpC'. Antimicrob Agents Chemother. Mar. 17, 2014. [Epub ahead of print] PubMed PMID: 24637685.

Snydman et al. 'Activity of Ceftolozane/Tazobactam Against a Broad Spectrum of Recent Clinical Anaerobic Isolates'. Antimicrob Agents Chemother. 2014 vol. 58, No. 2, pp. 1218-1223.

Zhanel et al. 'Ceftolozane/Tazobactam: A Novel Cephalosporin/β-Lactamase Inhibitor Combination with Activity Against Multidrug-Resistant Gram-Negative Bacilli'. Drugs. 2014 vol. 74 No. 1, pp. 31-51.

Vanscoy et al. 'Pharmacological basis of β-lactamase inhibitor therapeutics: tazobactam in combination with Ceftolozane'. Antimicrob Agents Chemother. 2013. vol. 57 No. 12, pp. 5924-5930.

Toda et al. 'FR264205, A Novel Parenteral Antipseudomonal Cephem: Synthesis and SAR of 3-(2,4-Disubstituted 3-Aminopyrazolio)methyl Cephalosporins'. 46th Annual Interscience Conference on Antimicrobial Agents and Chemotherapy (ICAAC 2006); Sep. 27-30, 2006; San Francisco, CA. Oral Presentation F1-0240.

Walkty et al. 'In vitro activity of ceftolozane-tazobactam against *Pseudomonas aeruginosa* isolates obtained from patients in Canadian hospitals in the CANWARD study, 2007 to 2012'. Antimicrob Agents Chemother. 2013, vol. 57, No. 11, pp. 5707-5709.

Hong et al. 'Ceftolozane/tazobactam: a novel antipseudomonal cephalosporin and β-lactamase-inhibitor combination'. Infect Drug Resist. 2013 vol. 29, No. 6, pp. 215-223.

Zilberberg et al. 'Prevalence of multidrug-resistant *Pseudomonas aeruginosa* and carbapenem-resistant Enterobacteriaceae among specimens from hospitalized patients with pneumonia and bloodstream infections in the United States from 2000 to 2009'. J Hosp Med. 2013 vol. 8, No. 10, pp. 559-563.

Zilberberg et al. 'Secular Trends in Gram-Negative Resistance among Urinary Tract Infection Hospitalizations in the United States, 2000-2009'. Infect Control Hosp Epidemiol. 2013, vol. 34, No. 9, pp. 940-946.

Hayakawa et al. 'Epidemiology and Risk Factors for Isolation of *Escherichia coli* Producing CTX-M-Type Extended-Spectrum β-Lactamase in a Large U.S. Medical Center'. Antimicrob Agents Chemother. 2013 vol. 57, No. 8, pp. 4010-4018.

Vanscoy et al. 'Relationship between Ceftolozane/Tazobactam Exposure and Drug-Resistance Amplification in a Hollow-Fiber Infection Model'. Antimicrob Agents Chemother. Jun. 17, 2013. [Epub ahead of print] PubMed PMID: 23774429.

Vanscoy et al. 'Pharmacokinetics-Pharmacodynamics of Tazobactam in Combination with Ceftolozane in an In Vitro Infection Model'. Antimicrob Agents Chemother. 2013 vol. 57, No. 6, pp. 2809-2814.

Craig et al. 'In-Vivo Activity of Ceftolozane, a New Cephalosporin, with and without Tazobactam against *Pseudomonas aeruginosa* and Enterobacteriaceae, including Strains with Extended-Spectrum β-Lactamases, in the Thighs of Neutropenic Mice'. Antimicrob Agents Chemother. 2013 vol. 57, No. 4, pp. 1577-1582.

Jacqueline et al. 'Efficacy of ceftolozane in a murine model of *Pseudomonas aeruginosa* acute pneumonia: in vivo antimicrobial activity and impact on host inflammatory response'. J Antimicrob Chemother. 2013 vol. 63, No. 1, pp. 177-183.

Miller et al. 'CXA-201 dose selection based on probability of target attainment and drug exposure in subjects with varying degrees of renal impairment'. 51st Annual Interscience Conference on Antimicrobial Agents and Chemotherapy (ICAAC 2011); Sep. 17-20, 2011; Chicago, IL. Oral Presentation A-1099.

Titelman et al. 'In vitro activity of CXA-101 plus tazobactam against CTX-M-14- and CTX-M-15-producing *Escherichia coli* and *Klebsiella pneumoniae*'. Diagn Microbiol Infect Dis. 2011 vol. 70, No. 1, pp. 137-141.

Ge et al. 'Pharmacokinetics and safety of CXA-101, a new antipseudomonal cephalosporin, in healthy adult male and female subjects receiving single- and multiple-dose intravenous infusions'. Antimicrob Agents Chemother. 2010 vol. 54, No. 8, pp. 3427-3431.

Juan et al. 'Activity of a new antipseudomonal cephalosporin, CXA-101, against carbapenem-resistant and multidrug-resistant *Pseudomonas aeruginosa* clinical strains'. Antimicrob Agents Chemother. 2010, vol. 54, No. 2, pp. 846-851.

Sader et al. 'Antimicrobial Activity of Ceftolozane/Tazobactam Tested Against Gram-Negative Bacterial Isolates from Hospitalized Patients with Pneumonia in European Hospitals (2011)'. 23rd Annual Meeting of the European Congress of Clinical Microbiology (ECCMID 2013); Apr. 27-30, 2013; Berlin, Germany. Oral Presentation O-181.

(56) References Cited

OTHER PUBLICATIONS

Nicasio et al. 'PK-PD of Tazobactam (TAZ) in Combination with Piperacillin (PIP) in an In Vitro Infection Model (IVIM)'. 53rd Annual Interscience Conference on Antimicrobial Agents and Chemotherapy (ICAAC 2013); Sep. 10-13, 2013; Denver, CO. Oral Presentation.

Ambrose, et al: Pharmacokinetic-pharmacodynamic considerations in the design of hospital-acquired or ventilator—associated bacterial pneumonia studies: look before you leap!; Clin Infect Dis, 2010, vol. 51, Suppl 1, pp. S103-S110.

American Thoracic Society; Infectious Diseases Society of America; Guidelines for the management of adults with hospital-acquired, ventilator-associated, and healthcare-associated pneumonia; Am J Respir Crit Care Med., 2005, vol. 171(4), pp. 388-416.

Baughman, et al: The diagnosis and treatment challenges in nosocomial pneumonia; Diagn Microbiol Infect Dis, vol. 33(2), pp. 131-139, 1999.

Bergogne-Berezin: Predicting the efficacy of antimicrobial agents in respiratory infections: is tissue concentration valid measure?; J Antimicrob Chemother, 1995, vol. 35, pp. 363-371.

Boselli, et al: Steady-state plasma and intrapulmonary concentrations of piperacillin/tazobactam 4 g10.5 g administered to critically ill patients with severe nosocomial pneumonia; Intensive Care Med, 2004, vol. 30, pp. 976-979.

Boselli, et al: Alveolar concentrations of piperacillin/tazobactam administered in continuous infusion to patients with—associated pneumonia; Crit Care Med, 2008, vol. 36, pp. 1500-1506.

Chastre, et al: Ventilator-associated pneumonia; Am J Respir Crit Care Med, 2002, vol. 165(7), pp. 867-903.

Chastre, et al: Comparison of 8 vs 15 days of antibiotic therapy for ventilator-associated pneumonia in adults: a randomized trial; JAMA, 2003, vol. 290(19), pp. 2588-2598.

El Solh: Update on the treatment of *Pseudomonas aeruginosa* pneumonia; J Antimicrob Chemother, 2009, vol. 64, pp. 229-238.

Freire, et al: Comparison of tigecycline with imipenem/cilastatin for the treatment of hospital-acquired penumonia; Diag Microbio and Infec Dis, 2010, vol. 68, pp. 140-151.

Harrison's Principles of Internal Medicine: Hospital-Acquired (Nosocomial) Pneumonia; ed. Kasper, et al.; 16th ed. New York: McGraw-Hill, Medical Pub. Division. 2005, pp. 1538-1541.

Jones, et al: Microbial etiologies of hospital-acquired bacterial pneumonia and ventilator-associated bacterial pneumonia; Clin Infect Dis; 2010, Suppl 1, pp. S81-S87.

Joseph, et al: Ventilator-associated pneumonia: A Review; EurJ Intern Med; 2010, vol. 21(5), pp. 360-368.

Klevens, et al: Estimating health care-associated infections and deaths in U.S. hospitals, 2002; Public Health Rep, 2007, vol. 122, pp. 160-166.

Knaus, et al: APACHE II: A severity of disease classification system; Crit Care Med, 1985, vol. 13, pp. 818-829.

Komuro, et al: Inhibition of the renal excretion of tazobactam by piperacillin; J Antimicrob Chemother, 1994, vol. 34, pp. 555-564.

Lucasti: A Phase 3, Randomized, Double-Blind Study of Ceftobiprole Medocaril Versus Linezolid Plus Ceftazidime in the Treatment of Nosocomial Pneumonia; Ceftobiprole: Clinical Study Report Synopsis BAP00248/307; Issue Date: Jul. 14, 2010; Document No. EDMS-PSDB-6906024:3.0, (8 pages).

Mesaros, et al: *Pseudomonas aeruginosa*: resistance and therapeutic options at the turn of the new millennium; Clin Microbiol Infect, 2007, vol. 13, pp. 560-578.

Occhipinti, et al: Pharmacokinetics and pharmacodynamics of two multiple-dose piperacillin-tazobactam regimens; Antimicrob Agents Chemother, 1997, vol. 41, pp. 2511-2517.

Pankey: Tigecycline; J Antimicrob Chemotherapy, 2005, vol. 56, pp. 470-480.

Pea: The antimicrobial therapy puzzle: could pharmacokinetic-pharmacodynamic relationships be helpful in addressing the issue of appropriate pneumonia treatment in critically ill patients?; Clin Infect Dis, 2006, vol. 42, pp. 1764-1771.

Richards, et al: Nosocomial infections in medical intensive care units in the United States. National Nosocomial Infections Surveillance System; Crit Care Med, 1999, vol. 27(5), pp. 887-892.

Schulgen, et al: Estimation of extra hospital stay attributable to nosocomial infections: heterogeneity and timing of events; J Clin Epidemiol; Apr. 2000, vol. 53(4), pp. 409-417.

Singh:et al: Short-course empiric antibiotic therapy for patients with pulmonary infiltrates in the intensive care unit. A proposed solution for indiscriminate antibiotic prescription; Am J Respir Crit Care Med, Aug. 2000, vol. 162(2, Pt 1), pp. 505-511.

Udy, et al: Augmented renal clearance: implications for antibacterial dosing in the critically ill; Clin Pharmacokinet, 2010, vol. 49(1), pp. 1-16.

Vincent, et al: Use of the SOFA score to assess the incidence of organ dysfunction/failure in intensive care units: results of a multicenter, prospective study. Working group on "sepsis-related problems" of the European Society of Intensive Care Medicine; Crit Care Med, 1998, vol. 26(11), pp. 1793-1800.

Wunderink, et al: Linezolid in methicillin-resistant *Staphylococcus aureus* nosocomial pneumonia: a randomized, controlled study; Clin Infect Dis, 2012, vol. 54(5), pp. 621-629.

Zilberberg, et al: Epidemiology of healthcare-associated pneumonia (HCAP); Semin Respir Crit Care Med, 2009, vol. 30, pp. 10-15.

Zosyn®. Prescribing Information. Wyeth Pharmaceuticals, Inc., Philadelphia, PA, USA; http://labeling.pfizer.com/showlabeling.aspx?id=416 (Apr. 23, 2012, date last accessed), 26 pages.

Committee for Medicinal Products for Human Use (CHMP). Guideline on reporting the results of population pharmacokinetic analyses. European Medicines Agency Web site. http://www.ema.europa.eu/docs/en_GB/document_library/Scientific_guideline/2009/09/WC500003067.pdf. Accessed May 29, 2014.

Cockcroft et al. 'Prediction of Creatinine Clearance from Serum Creatinine'. Nephron. 1976, vol. 16, No. 1, pp. 31-41.

Yano et al. 'Evaluating Pharmacokinetic/Pharmacodynamic Models Using the Posterior Predictive Check'. J Pharmacokinet Pharmacodyn. 2001, vol. 28, No. 2, pp. 171-192.

Adnan et al. 'Pharmacokinetics of Beta-lactam Antibiotics in Patients with Intra-abdominal Disease: A Structured Review'. Surg Infect. 2012, vol. 13, No. 1, pp. 9-17.

Concordt et al. Population PK/PD analysis. New York, NY: Marcel Dekker, Inc; 2004.

Goncalves-Pereira et al. 'Antibiotics in Critically Ill Patients: A Systematic Review of the Pharmacokinetics of Beta-lactams'. Crit. Care. 2011, vol. 15, No. 5, pp. R206.

Udy et al. 'How Should We Dose Antibiotics for Pneumonia in the ICU?' Current Opinion in Infectious Diseases. 2013, vol. 26, No. 2, pp. 189-195.

Freeman et al. 'Once-Daily Dosing of Aminoglycosides: Review and Recommendations for Clinical Practice'. J. Antimicrob. Chemotherapy. 1997, vol. 39, No. 6, pp. 677-686.

McKindley et al. Chapter 41: Drug Use in the Critically Ill Patient with Renal Dysfunction-Application of the DREM System, in Infectious Diseases in Critical Care Medicine (DTX-355). Copyright 1998.

Mutschler et al. Chapter 2: Pharmacokinetics in Drug Actions: Basic Principles and Therapeutic Aspects. Medpharm Scientific Publishers, Stuttgart, Germany p. 5-47 (DTX-371). Copyright 1995.

Rotschafer et al. 'Therapeutic Update on Glycopeptide and Lipopeptide Antibiotics' Pharmacotherapy. 1988, vol. 8, No. 4, pp. 211-219.

Arin et al, 'The Comparative Stability of Different Types of Penicillin and Cephalosporin N-pyrryl derivatives'. Pharmazie 1988, vol. 43, pp. 18-19.

Cefazolin, (For Injection USP) Approved Dec. 1988, Product Label, B. Braun Medical Inc. Revised Jan. 2012.

Ceftazidime, (Systemic) Approved Nov. 1985, Product Label. American Society of Health-System Pharmacists Inc. 2004.

Claforan, (Sterile—Cefotaxime for injection, USP & Injection—Cefotaxime injection) Approved Prior to Jan. 1982, Product Label. Sanofi-Aventis U.S. LLC 2011.

Cubist Pharmaceuticals, 'Cubist Announces Positive Results from Two Phase 2 Trials, CXA-201 and CDAD Program'. Cubist Press Release. Jun. 2011.

(56) References Cited

OTHER PUBLICATIONS

Doribax, Approved Oct. 2007, Product Label. Ortho-McNeil-Janssen Pharmaceuticals, Inc. 2007.

Fortaz, (ceftazidime for Injection) (Ceftazidime Injection) Approved Jul. 1985, Product Label. GlaxoSmithKline 2007.

Maxipime, (Cefepime Hydrochloride, USP) Approved Jan. 1996, Product Label. Bristol-Myers Squibb Company, Revised Mar. 2009.

Yamana et al, 'Comparative Stability of Cephalosporins in Aqueous Solution: Kinetics and Mechanisms of Degradation'. Journal of Pharmaceutical Sciences 1976, vol. 65, No. 11, pp. 1563-1574.

Rocephin, (Ceftiaxone Sodium) Approved Aug. 1993, Product Label. Roche Laboratories, Copyright 1998.

Zithromax, (azithromycin injection) Approved Sep. 1994, Product Label. Pfizer Labs, Revised Feb. 2013.

Teflaro, (Ceftaroline fosamil) Approved Oct. 2010, Product Label. Forst Laboratories, Inc. 2010.

Abstract for Sader et al. 'Antimicrobial Activity of Ceftolozane/Tazobactam Tested Against Gram-negative Bacterial Isolates from Hospitalized Patients with Pneumonia in United States (USA) and European (EU) Hospitals (2012)'. 53rd Annual Interscience Conference on Antimicrobial Agents and Chemotherapy (ICAAC 2013); Sep. 10-13, 2013; Denver, CO. Poster C2-1633.

Abstract for Sader et al. 'Post Beta-Lactamase Inhibitor Effect of Tazobactam When Associated with Ceftolozane and Tested against ESBL-Producing Strains'. 53rd Annual Interscience Conference on Antimicrobial Agents and Chemotherapy (ICAAC 2013); Sep. 10-13, 2013; Denver, CO. Poster A-1030.

Abstract for Vanscoy et al. 'Relationship between Ceftolozane/Tazobactam (TOL/TAZ) Exposure and *E. coli* Resistance Amplification Prevention in a Hollow Fiber Infection Model (HFIM)'. 53rd Annual Interscience Conference on Antimicrobial Agents and Chemotherapy (ICAAC 2013); Sep. 10-13, 2013; Denver, CO. Poster A-1031.

Abstract for Vanscoy et al. 'Identification of a Translational Relationship Between Tazobactam (TAZ) Exposure in Combination with Ceftolozane (TOL) and Efficacy Against ESBL-Producing Enterobacteriaceae'. 53rd Annual Interscience Conference on Antimicrobial Agents and Chemotherapy (ICAAC 2013); Sep. 10-13, 2013; Denver, CO. Poster A-1032.

Abstract for Zhanel et al. 'In Vitro Activity of Ceftolozane/Tazobactam Against 5,715 Gram-Negative and Gram-Positive Pathogens Isolated from Patients in Canadian Hospitals in 2011 and 2012: CANWARD Surveillance Study'. 53rd Annual Interscience Conference on Antimicrobial Agents and Chemotherapy (ICAAC 2013); Sep. 10-13, 2013; Denver, CO. Poster E-1689.

Abstract for Zilberberg et al. 'Multidrug resistant *Pseudomonas aeruginosa* among hospitalized patients with pneumonia, US 2000-2009'. Making a Difference in Infectious Diseases Pharmacotherapy Conference (MAD-ID 2013); May 9-11, 2013; Orlando, FL. Encore Presentation from ISICEM 2013. Poster #75.

Abstract for Zilberberg et al. 'Gram-negative resistance and need for ICU among urinary tract infections in the US'. Making a Difference in Infectious Diseases Pharmacotherapy Conference (MAD-ID 2013); May 9-11, 2013; Orlando, FL. Encore Presentation from ISICEM 2013. Poster #74.

Abstract for Zilberberg et al. 'Multidrug resistance among *P. aeruginosa* and Enterobacteriaceae in the US hospitals, 2000-2009'. Making a Difference in Infectious Diseases Pharmacotherapy Conference (MAD-ID 2013); May 9-11, 2013; Orlando, FL. Encore Presentation from SCCM 2013.

Abstract for Chandorkar et al. 'Target Attainment Rates (TAR) and Cumulative Fraction of Response (CFR) in Plasma for Ceftolozane in a Simulated Population of Patients with Complicated Intra-abdominal (cIAI) and Urinary Tract Infection (cUTI)'. 23rd Annual Meeting of the European Congress of Clinical Microbiology (ECCMID 2013); Apr. 27-30, 2013; Berlin, Germany. Poster P2742.

Abstract for Halimi et al. 'Comparative Evaluation of Ceftolozane/tazobactam MIC testing with Etest® and CLSI Broth Microdilution Methods'. 23rd Annual Meeting of the European Congress of Clinical Microbiology (ECCMID 2013); Apr. 27-30, 2013; Berlin, Germany. Poster P1606.

Abstract for Reynolds et al. '*Pseudomonas aeruginosa* in the UK and Ireland: Susceptibility to Old and New Agents'. 23rd Annual Meeting of the European Congress of Clinical Microbiology (ECCMID 2013); Apr. 27-30, 2013; Berlin, Germany. Poster P1519.

Abstract for Sader et al. 'Antimicrobial activity of ceftolozane/tazobactam and comparator agents tested against *Pseudomonas aeruginosa* strains from 14 European countries and Israel'. 23rd Annual Meeting of the European Congress of Clinical Microbiology (ECCMID 2013); Apr. 27-30, 2013; Berlin, Germany. Poster P337.

Abstract for Noel et al. 'Pharmacodynamics of Ceftolozane/Tazobactam Against Gram Negative Bacilli'. 53rd Annual Interscience Conference on Antimicrobial Agents and Chemotherapy (ICAAC 2013); Sep. 10-13, 2013; Denver, CO. Poster A1029.

Abstract for Melchers et al. 'Pharmacokinetics of Tazobactam and Ceftolozane Alone and in Combination in Mice'. 53rd Annual Interscience Conference on Antimicrobial Agents and Chemotherapy (ICAAC 2013); Sep. 10-13, 2013; Denver, CO. Poster A-1033.

Abstract for Melchers et al. 'Pharmacodynamics of Ceftolozane Combined with Tazobactam in a Neutropenic Mouse Thigh Model'. 53rd Annual Interscience Conference on Antimicrobial Agents and Chemotherapy (ICAAC 2013); Sep. 10-13, 2013; Denver, CO. Poster A-1034.

Abstract for Lucasti et al. 'A Multicenter, Double-Blind, Randomized, Phase 2 Study to Assess the Safety and Efficacy of Ceftolozane/Tazobactam (TOL/TAZ) plus Metronidazole (MTZ) Compared to Meropenem (MER) in Adult Patients with Complicated Intra-abdominal Infections (cIAI)'. 53rd Annual Interscience Conference on Antimicrobial Agents and Chemotherapy (ICAAC 2013); Sep. 10-13, 2013; Denver, CO. Poster K-1709.

Abstract for Estabrook et al. 'In vitro Activity of CXA-201 (Ceftolozane-Tazobactam) Against 200 CTX M-Producing *Escherichia coli* Clinical Isolates'. 53rd Annual Interscience Conference on Antimicrobial Agents and Chemotherapy (ICAAC 2013); Sep. 10-13, 2013; Denver, CO. Poster E-1169.

Abstract for Bulik et al. 'In vitro activity of CXA-101, a novel cephalosporin, against resistant phenotypes of *Pseudomonas aeruginosa*'. 47th Annual Meeting of the Infectious Diseases Society (IDSA 2009); Oct. 29-Nov. 1 2009; Philadelphia, PA. Poster 209.

Abstract for Moya et al. 'Activity of CXA-101 against *Pseudomonas aeruginosa* beta-lactam resistance mechanisms: ampD, ampDh2, ampDh2, dacB, and oprD mutations'. 49th Annual Interscience Conference on Antimicrobial Agents and Chemotherapy (ICAAC 2009); Sep. 12-15, 2009; San Francisco, CA. Poster F1-1989.

Abstract for Livermore et al. 'Chequerboard titrations of cephalosporin CXA-101 and tazobactam vs. beta-lactamase producing Enterobacteriaceae'. 49th Annual Interscience Conference on Antimicrobial Agents and Chemotherapy (ICAAC 2009); Sep. 12-15, 2009; San Francisco, CA. Poster F1-1994.

Abstract for Jacqueline et al. 'ED50 Determination of CXA-101 Alone and in Combination with Tazobactam for Treating Experimental Peritonitis in Mice Due to ESBL-Producing *Klebsiella pneumoniae* strains: Comparison with Ceftazidime and Piperacillin/Tazobactam'. 50th Annual Interscience Conference on Antimicrobial Agents and Chemotherapy (ICAAC 2010); Sep. 12-15, 2010; Boston, MA. Poster B-708.

Abstract for Cabot et al. '*Pseudomonas aeruginosa* Ceftolozane/Tazobactam Resistance Development Requires Multiple Mutations Leading to Overexpression and Structural Modification of AmpC'. 53rd Annual Interscience Conference on Antimicrobial Agents and Chemotherapy (ICAAC 2013); Sep. 10-13, 2013; Denver, CO. Poster C1-060.

Abstract for Jacqueline. 'In vivo Activity of CXA-101 against *Pseudomonas aeruginosa* in a Rabbit Experimental Pneumonia: Comparison with Ceftazidime Piperacillin-Tazobactam and Imipenem'. 51st Annual Interscience Conference on Antimicrobial Agents and Chemotherapy (ICAAC 2011); Sep. 17-20, 2011; Chicago, IL. Poster B-590.

Abstract for Reynolds et al. 'Enterobacteriaceae in the UK and Ireland: Susceptibility to Old and New Agents'. 52nd Annual

(56) References Cited

OTHER PUBLICATIONS

Interscience Conference on Antimicrobial Agents and Chemotherapy (ICAAC 2012); Sep. 9-12, 2012; San Francisco, CA. Poster C2-152.
Abstract for Miller et al. 'Safety and Pharmacokinetics of Intravenous Ceftolozane/tazobactam 3 g every 8 Hours and Cumulative Fraction of Response in Plasma and Epithelial Lining Fluid in a Simulated Ventilator Associated Pneumonia Population'. 52nd Annual Interscience Conference on Antimicrobial Agents and Chemotherapy (ICAAC 2012); Sep. 9-12, 2012; San Francisco, CA. Poster A-624.
Abstract for Melchers et al. 'In vitro Activity of CXA-101 Alone and in Combination With Tazobactam Against Extended Spectrum Beta-lactamase Harbouring Enterobacteriaceae'. 52nd Annual Interscience Conference on Antimicrobial Agents and Chemotherapy (ICAAC 2012); Sep. 9-12, 2012; San Francisco, CA. Poster E 198.
Abstract for Zilberberg et al. 'Prevalence of beta-lactam resistance among *P. aeruginosa* in US hospitals, 2000-2009'. To be presented at the 2nd Annual IDWeek (IDWeek 2013); Oct. 2-6, 2013; San Francisco, CA. Poster #1580.
Abstract for Cabot et al. 'Dynamics and mechanisms of resistance development to ceftazidime, meropenem and ceftolozane-/tazobactam in wild-type and mutator *P. aeruginosa* strains'. 52nd Annual Interscience Conference on Antimicrobial Agents and Chemotherapy (ICAAC 2012); Sep. 9-12, 2012; San Francisco, CA. Poster C1-1970.
Abstract for Sader et al. 'Frequency of occurrence and antimicrobial susceptibility of Gram-negative organisms isolated from health care associated urinary tract infections: Results from the Program to Assess Ceftolozane/Tazobactam Susceptibility (PACTS)'. To be presented at the 2nd Annual IDWeek (IDWeek 2013); Oct. 2-6, 2013; San Francisco, CA. Poster. 699.
Abstract for Zilberberg et al. 'Secular trends in gram-negative resistance among urinary tract infection hospitalizations in the US, 2000-2009'. 23rd Annual Meeting of the European Congress of Clinical Microbiology (ECCMID 2013); Apr. 27-30, 2013; Berlin, Germany. Poster P1517.
Abstract for Vanscoy et al. 'Pharmacokinetics-Pharmacodynamics (PK-PD) of Tazobactam in Combination with Ceftolozane in an In Vitro Infection Model'. 23rd Annual Meeting of the European Congress of Clinical Microbiology (ECCMID 2013); Apr. 27-30, 2013; Berlin, Germany. Poster P900.
Abstract for Sader et al. 'Ceftolozane/tazobactam activity tested against aerobic Gram-negative organisms isolated from intraabdominal infections in European and United States hospitals (2012)'. To be presented at the 2nd Annual IDWeek (IDWeek 2013); Oct. 2-6, 2013; San Francisco, CA. Poster #698.
Abstract for Sader et al. 'Antimicrobial susceptibility of gram-negative bacteria causing urinary tract infections in European and United States hospitals (2009-2011)'. 23rd Annual Meeting of the European Congress of Clinical Microbiology (ECCMID 2013); Apr. 27-30, 2013; Berlin, Germany. Poster P1516.
Abstract for Chandorkar et al. 'Population Pharmacokinetics (PPK) Meta-Analysis of Ceftolozane/Tazobactam in Healthy Volunteers and Patients'. Presented at the Annual Meeting of the American College of Clinical Pharmacy (ACCP 2013); Oct. 13-16, 2013; Albuquerque, NM. Poster # 120.
Abstract for Chandorkar et al. 'Pharmacokinetics and Safety of Ceftolozane/Tazobactam in Subjects with Severe Renal Impairment or End Stage Renal Disease on Hemodialysis'. To be presented at the 2nd Annual IDWeek (IDWeek 2013); Oct. 2-6, 2013; San Francisco, CA. Poster #723.
36 Abstract for Sader et al. 'Antimicrobial activity of ceftolozane/tazobactam and comparator agents tested against *Pseudomonas aeruginosa* isolates from United States (USA) medical centers (2011-2012)'. To be presented at the 2nd Annual IDWeek (IDWeek 2013); Oct. 2-6, 2013; San Francisco, CA. Poster #695.
Anderegg et al: Quality Control Guidelines for BAL9141 (Ro 63-9141), an Investigational Cephalosporin, When Reference MIC and Standardized Disk Diffusion Susceptibility Test Methods are Used; Journal of Clinical Microbiology. (2004), pp. 3356-3358.
Farrell: Antimicrobial Activity of Ceftolozane-Tazobactam Tested against Enterobacteriaceae with Various Resistance Patterns Isolated in U.S. Hospitals; Antimicrobial Agents and Chemotherapy; (2013) vol. 57 No. 12 pp. 6305-6310.
International Preliminary Report on Patentability for for PCT/US2012/054191, dated Mar. 12, 2014, 8 pages.
International Search Report for PCT/US2012/054191, dated Feb. 20, 2013, 4 pages.
Marunaka: Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 44-dioxide (YTR-830H), in Aqueous Solutions and Alkaline MEthanol Solution: Pathway and Structural Elucidation of Products; Chem. Pharm. Bull.; 1988, vol. 36, pp. 4478-4487.
Matsushima: Degradation of beta-lactamase inhibitor, (2S,3R,5S)-3-methyl-7-oxo-3-(1H-1,2,3-triazol-1-yl-methyl)-4-thia-1-azabicyclo[3.2.0]heptane-2-carboxylic acid 44-dioxide (YTR-830H) in Solid State: Structural Eldcidation; Chem. Pharm. Bull.; 1988, vol. 36, pp. 4593-4596.
Murano: Structural requirements for the stability of novel cephalosporins to AmpC beta-lactamase based on 3-D structure; Bioorg. Med. Chem. Lett.; 2007, vol. 16, pp. 2261-2275.
Search Request Confirmation; Science IP; Dec. 6, 2010, 3 pages.
Sutcliffe et al: Multidrug-Resistant Gram-Negative Pathogens: New Strategies; Tetraphase Pharmaceuticals . Retrieved online from: http://www.tufts.edu/med/apua/practitioners/resources_23_2817980013.pdf Retrieved Mar. 19, 2014.
U.S. National Institutes of Health, 'Safety and Efficacy Study of Ceftolozane/Tazobactam to Treat Ventilated Nosocomial Pneumonia (ASPECT-NP)'. Sponsored by Cubist Pharmaceuticals. http://www.clinicaltrials.gov/ct2/show/NCT02070757?term=ceftolozane&rank=1 Updated Feb. 21, 2014. ClinicalTrials.gov Identifier: NCT02070757 (Study not yet open for participant recruitment).
U.S. National Institutes of Health, 'Safety and Efficacy Study of IV CXA-101 and IV Ceftazidime in Patients with Complicated Urinary Tract Infections'. Sponsored by Cubist Pharmaceuticals. http://www.clinicaltrials.gov/ct2/show/NCT00921024?term=ceftolozane&rank=4 Updated Aug. 5, 2010. ClinicalTrials.gov Identifier: NCT00921024 (Study has been completed).
U.S. National Institutes of Health, 'Safety and Efficacy Study to Compare IV CXA 101/Tazobactam and Metronidazole With Meropenem in Complicated Intraabdominal Infections'. Sponsored by Cubist Pharmaceuticals. http://www.clinicaltrials.gov/ct2/show/NCT01147640?term=ceftolozane&rank=2 Updated May 5, 2011. ClinicalTrials.gov Identifier: NCT01147640 (Study has been completed).
U.S. National Institutes of Health, 'Study of Intravenous Ceftolozane/Tazobactam vs. Piperacillin/Tazobactam in Ventilator Associated Pneumonia'. Sponsored by Cubist Pharmaceuticals. http://www.clinicaltrials.gov/ct2/show/NCT01853982?term=ceftolozane&rank=3 Updated Jan. 28, 2014. ClinicalTrials.gov Identifier: NCT01853982 (Study has been terminated).
Wootton et al: BAL 9141, a new borad-spectrum pyrrolidinone cephalosporin: activity against clinically significant anaerobes in comparison with 10 other antimicrobials; Journal of Antimicrobial Chemotherapy; (2002) vol. 49, pp. 535-539.
Written Opinion of the International Searching Authority for PCT/US2012/054191, dated Feb. 20, 2013, 7 pages.
Yoshizawa: New broad-spectrun parenteral cephalosporins exhibiting potent activity against both methicilln-resistant *Staphlococcus aureus* (MRSA) and *Pseudomonas aeruginosa*. Part 3: &Beta-[2-(5-Amino-1,2,4-thiadiazol-3-yl)-2-ethoxtiminoacetamido] cephalosporins bearing 4[3-(aminoalkyl)-ureido]-1-pyridinium at C3; Bioorg. Med. Chem. Lett.; 2004, vol. 12, pp. 4221-4231.
Brown, R.F. et al. 'Synthesis and Biological Evaluation of a Series of Parental 3'-Quaternary Ammonium Cephalosporins.sup.1' Journal of Medicinal Chemistry. 1990, vol. 33, No. 8, pp. 2114-2121.
Sakagami, K. et al. 'Synthetic Cephalosporins. VI..sup.1) Synthesis and Antibacterial Activity of 7-[(Z)-2-(2-Aminothiazol-4-YL)-2-(1-Carboxy-1-Methyl)Ethoxyiminoacetamido-   ]-3-(3-Hydroxy-4-

(56) References Cited

OTHER PUBLICATIONS

Pyridon-1-YL)Methyl-3-Cephem-4-Carboxylic Acid and Related Compounds'. Chemical and Pharmaceutical Bulletin. 1990, vol. 38, No. 8, pp. 2271-2273.
English Translation of Abstract for Japanese Patent No. JP 04-288286, published Oct. 13, 1992, 3 pages.
European Committee on Antimicrobial Sus Testing 2012.
Giske et al, 'Activity of Cephalosporin CXA-101 and Comparators against Extended-spectrum-beta-lactamase—producing *Pseudomonas aeruginosa*'. Journal of Antimicrobial Chemotherapy 2009, vol. 64, No. 2, pp. 430-431.
Jacqueline et al, 'Efficacy of Ceftolozane in a Murine Model of *Pseudomonas aeruginosa* acute pneumonia: in vivo Antimicrobial Activity and Impact on Host Inflammatory Response'. Journal of Antimicrobial Chemotherapy 2012, vol. 68, No. 1, pp. 1-7.
Livermore et al, 'Activity of Cephalosporin CXA-101 against *Pseudomonas aeruginosa* and *Burkholderia cepacia* strains and Isolates'. International Journal of Antimicrobial Agents 2009, vol. 34, No. 5, pp. 402-406.
Takeda et al, 'Stability of FR264205 against AmpC beta-lactamase of *Pseudomonas aeruginoas*'. International Journal Antimicrobial Agents, 2007. vol. 30, No. 5, pp. 443-445.
Takeda et al., In vitro and in vivo activities of a new cephalosporin, FR264205, against *Pseudomonas aeruginosa*. Antimicrob Agents Chemother. 2007; 51(3):826-30.
Titelman et al, 'In vitro Activity of CXA-101 Plus Tazobactum against CTX-M-14 and CTX-M-15-producing *Escherichia* and *Klebsiella pneumoniae*'. Diagnostic Microbiology and Infectious Disease. 2011, vol. 70, No. 1, pp. 137-141.
Toda et al, Synthesis and SAR of Novel Parenteral Anti-pseudomonal cephalosporins: Discovering of FR264205. Med Chem Lett. 2008, vol. 18, No. 17, pp. 4849-4852.
U.S. Appl. No. 14/020,230, filed Sep. 6, 2013.
U.S. Appl. No. 14/020,212, filed Sep. 6, 2013.
U.S. Appl. No. 14/200,383, filed Mar. 14, 2014.
U.S. Appl. No. 14/211,216, filed Mar. 14, 2014.
U.S. Appl. No. 14/211,229, filed Mar. 14, 2014.
U.S. Appl. No. 14/211,465, filed Mar. 14, 2014.
U.S. Appl. No. 14/211,526, filed Mar. 14, 2014.
U.S. Appl. No. 14/212,781, filed Mar. 14, 2014.
U.S. Appl. No. 14/214,212, filed Mar. 14, 2014.
U.S. Appl. No. 14/214,324, filed Mar. 14, 2014.
U.S. Appl. No. 14/213,532, filed Mar. 14, 2014.
U.S. Appl. No. 14/212,590, filed Mar. 14, 2014.
U.S. Appl. No. 14/214,221, filed Mar. 14, 2014.
U.S. Appl. No. 14/214,417, filed Mar. 14, 2014.
U.S. Appl. No. 14/214,367, filed Mar. 14, 2014.
U.S. Appl. No. 14/213,997, filed Mar. 14, 2014.
U.S. Appl. No. 14/212,625, filed Mar. 14, 2014.
U.S. Appl. No. 14/214,260, filed Mar. 14, 2014.
Non-Final Office Action issued for U.S. Appl. No. 14/214,234, mailed Jul. 7, 2014 (16 pages).

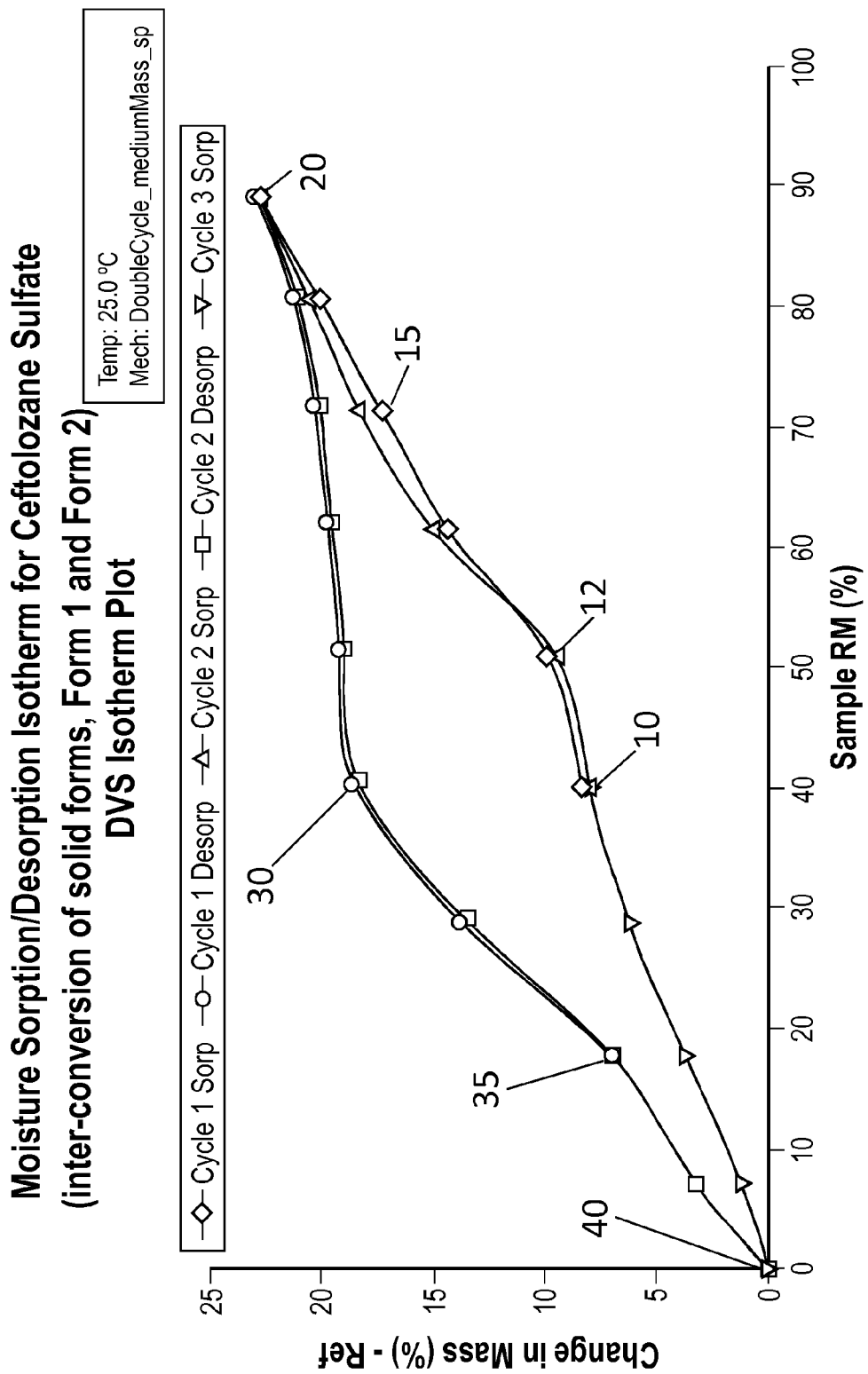

SOLID FORMS OF CEFTOLOZANE

RELATED APPLICATIONS

This application claims priority to U.S. Provisional Patent Application No. 61/883,530, filed Sep. 27, 2013, which is incorporated herein in its entirety.

TECHNICAL FIELD

This disclosure relates to solid forms of ceftolozane.

BACKGROUND

The crystal state of a compound may be important when the compound is used for pharmaceutical purposes. Compared with an amorphous solid, the solid physical properties of a crystalline compound may change from one solid form to another, which may affect its suitability for pharmaceutical use. In addition, different solid forms of a crystalline compound can incorporate different types and/or different amounts of impurities. Different solid forms of a compound can also have different chemical stability upon exposure to heat and/or water over a period of time.

Ceftolozane is a cephalosporin antibacterial agent, also referred to as CXA-101, FR264205, or by chemical names such as (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate. Ceftolozane sulfate is a pharmaceutically acceptable ceftolozane salt of formula (I) that can be formulated for intravenous administration or infusion.

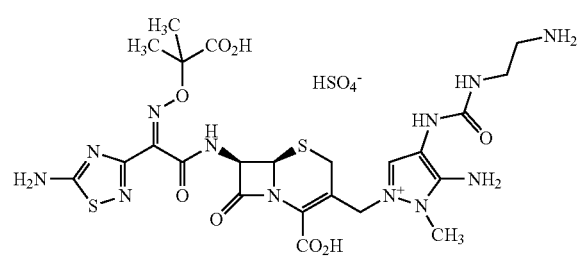

(I)

U.S. Pat. No. 7,129,232 discloses ceftolozane hydrogen sulfate salt among other salts "with a base or an acid addition salt such as a salt with an inorganic base, for example, an alkali metal salt [e.g., sodium salt, potassium salt, etc.], an alkaline earth metal salt [e.g., calcium salt, magnesium salt, etc.], an ammonium salt; a salt with an organic base, for example, an organic amine salt [e.g., trimethylamine salt, triethylamine salt, pyridine salt, picoline salt, ethanolamine salt, triethanolamine salt, dicyclohexylamine salt, N,N'-dibenzylethylenediamine salt, etc.]; an inorganic acid addition salt [e.g., hydrochloride, hydrobromide, sulfate, hydrogen sulfate, phosphate, etc.]; an organic carboxylic or sulfonic acid addition salt [e.g., formate, acetate, trifluoroacetate, maleate, tartrate, citrate, fumarate, methanesulfonate, benzenesulfonate, toluenesulfonate, etc.]; and a salt with a basic or acidic amino acid [e.g., arginine, aspartic acid, glutamic acid, etc.]." In addition, U.S. Pat. No. 7,129,232 discloses a crystal solid form of ceftolozane sulfate obtained by dissolving ceftolozane sulfate in a solution of water and ethanol, adding seed crystals, to obtain the crystal form described herein as (Comparative) Example 1. A synthesis of ceftolozane is also described in U.S. Pat. No. 7,129,232.

As reported herein, there remains a need for solid forms of ceftolozane having improved ceftolozane stability. For example, the purity of ceftolozane in an aqueous ethanol solution during precipitation according to the methods of U.S. Pat. No. 7,129,232 decreased from about 97% to about 68% during a 6-day stability test (See Example 3), as measured by high performance liquid chromatography (HPLC). Accordingly, there remains a need for solid forms of ceftolozane greater ceftolozane stability for use in drug substance and drug product development.

SUMMARY

Novel solid forms of ceftolozane (e.g., crystalline ceftolozane sulfate) disclosed herein include ceftolozane sulfate in Form 1 and Form 2, as well as compositions comprising a solid form of ceftolozane comprising at least one or more of ceftolozane sulfate Form 1 and ceftolozane sulfate Form 2. Novel compositions also include ceftolozane sulfate solid Form 1, ceftolozane sulfate solid Form 2 and/or crystalline and amorphous solid forms of ceftolozane. A novel ceftolozane solid Form 1 and a novel ceftolozane solid Form 2 of ceftolozane sulfate can both be identified by X-ray Powder Diffraction (XRPD), both having one or more characteristic diffractions at angles (2 theta±0.2) of 24.2 and 37.8. In addition, ceftolozane diffractions in both solid Form 1 and solid Form 2 can produce the Raman spectra comprising one or more of the following peaks (+/−5 cm$^{-1}$) at about 597 cm$^{-1}$, 716 cm$^{-1}$, and 1329 cm$^{-1}$. A preferred ceftolozane composition can include ceftolozane in one or more solid forms (e.g., solid Form 1 and/or solid Form 2) characterized by an XRPD pattern with diffractions at angles (2 theta±0.2) of 24.2 and 37.8, in addition to Raman spectra comprising one or more of the following peaks at about 597 cm$^{-1}$, 716 cm$^{-1}$, and 1329 cm$^{-1}$.

A novel ceftolozane solid Form 1 of ceftolozane sulfate can be identified by X-ray Powder Diffraction (XRPD), having one or more characteristic diffractions at angles (2 theta±0.2) of 12.4, 16.4, 22.6, 25.1, and 28.0. In addition, ceftolozane in solid Form 1 can produce the Raman spectra comprising one or more of the following peaks (+/−5 cm$^{-1}$) at 171 cm$^{-1}$, 743 cm$^{-1}$, 819 cm$^{-1}$, 1055 cm$^{-1}$, 2894 cm$^{-1}$, and 2976 cm$^{-1}$.

A novel ceftolozane solid Form 2 of ceftolozane sulfate can be identified by X-ray Powder Diffraction (XRPD), having one or more characteristic diffractions at angles (2 theta±0.2) of 4.4, 8.8, 11.0, 14.9, and 17.7. In addition, ceftolozane in solid Form 1 can produce the Raman spectra comprising one or more of the following peaks (±5 cm$^{-1}$) at 151 cm$^{-1}$, 684 cm$^{-1}$, 802 cm$^{-1}$, 1174 cm$^{-1}$, and 2953 cm$^{-1}$.

The applicants have also discovered that novel ceftolozane salt solid forms (e.g., Form 1 and Form 2 of ceftolozane sulfate) can also be obtained by maintaining a ceftolozane salt solid form under physical conditions effective to convert a ceftolozane salt in a first solid form into a ceftolozane salt in a second solid form. For example, performing a water sorption isotherm (e.g., FIG. 5) of ceftolozane sulfate in Form 1 showed a reversible transformation between ceftolozane sulfate in solid Form 1 and solid Form 2 as a function of relative humidity. The solid form of ceftolozane can be changed by maintaining the ceftolozane at certain relative humidity conditions (e.g., as described in the water sorption isotherm for ceftolozane sulfate in FIG. 5). Ceftolozane in solid Form 2 can be converted to ceftolozane in Form 1 by maintaining a sample at a relative humidity (RH) effective to convert ceftolozane in Form 2 to ceftolozane into Form 1 at a suitable temperature (e.g., RH of about 50% or higher at a temperature of about 20-25 degrees C., preferably at least about 70% RH at a temperature of about 25 degrees C.). Once formed in this manner, ceftolozane in solid Form 1 can be converted to ceftolozane sulfate in Form 2 by reducing the RH (e.g., RH of about 20-40%). The ceftolozane sulfate in Form 2 can be converted to a mixture of amorphous ceftolozane sulfate and Form 2 by reducing the RH to less than about 20%.

The ceftolozane solid forms (Form 1 and Form 2) can be obtained from a solution comprising isopropanol, or by maintaining a ceftolozane solid form under conditions effective to convert a first solid form into a second solid form (e.g., by maintaining ceftolozane sulfate in Form 1 under physical conditions effective to form ceftolozane sulfate in Form 2, or converting Form 2 under physical conditions effective to form ceftolozane sulfate of Form 1). An improved manufacturing method can include the steps of (a) combining ceftolozane sulfate with a molar excess of sulfuric acid (e.g., about 2.5 molar equivalents of sulfuric acid to ceftolozane) and isopropanol (e.g., about 20-40 volumes of isopropanol relative to the amount of ceftolozane active) under conditions effective to produce a ceftolozane solid form (e.g., ceftolozane sulfate Form 1), and (b) isolating the ceftolozane solid form (e.g., by filtering the ceftolozane solid form from a solution comprising the isopropanol).

The applicants have discovered novel methods of manufacturing ceftolozane sulfate solid forms that provide improved ceftolozane stability during manufacturing compared to the methods of manufacturing ceftolozane solid forms disclosed in U.S. Pat. No. 7,129,232 (see Comparative Example 1 herein). The improved manufacturing methods are based in part on the discovery that solid forms of ceftolozane sulfate obtained by certain processes comprising the use of isopropanol (e.g., as described in Example 2a) with ceftolozane provide improved ceftolozane stability in a liquid phase during manufacturing (compared to the manufacturing methods described in U.S. Pat. No. 7,129,232), as measured by a ceftolozane purity of about 82% after a 6-day ceftolozane stability test of Example 3 (compared to about 68% from ceftolozane solid forms disclosed in U.S. Pat. No. 7,129,232). The novel ceftolozane solid forms, including ceftolozane sulfate solid Form 1 and ceftolozane solid Form 2, can be obtained from an aqueous solution with isopropyl alcohol, even in the absence of ethanol. In contrast, U.S. Pat. No. 7,129,232 discloses a ceftolozane solid form obtained from an aqueous solution without isopropyl alcohol.

The manufacturing methods are useful for the manufacture of antibiotic compositions comprising ceftolozane in one or more solid forms suitable for treatment of infections. For example, a pharmaceutical composition comprising ceftolozane for parenteral administration can be obtained from ceftolozane sulfate in solid Form 1 and/or solid Form 2 by a process comprising the steps of: (a) forming a ceftolozane solution comprising ceftolozane sulfate in a solid Form 1 and/or solid Form 2, and (b) lyophilizing the ceftolozane solution to obtain a lyophilized ceftolozane composition. The lyophilized ceftolozane composition can be combined with tazobactam (or a pharmaceutically acceptable salt thereof) to obtain a CXA-201 pharmaceutical composition suitable for intravenous administration upon reconstitution.

BRIEF DESCRIPTION OF THE DRAWINGS

FIG. 5 is a moisture sorption/desorption isotherm for ceftolozane sulfate solid forms.

DETAILED DESCRIPTION

Figure 1:
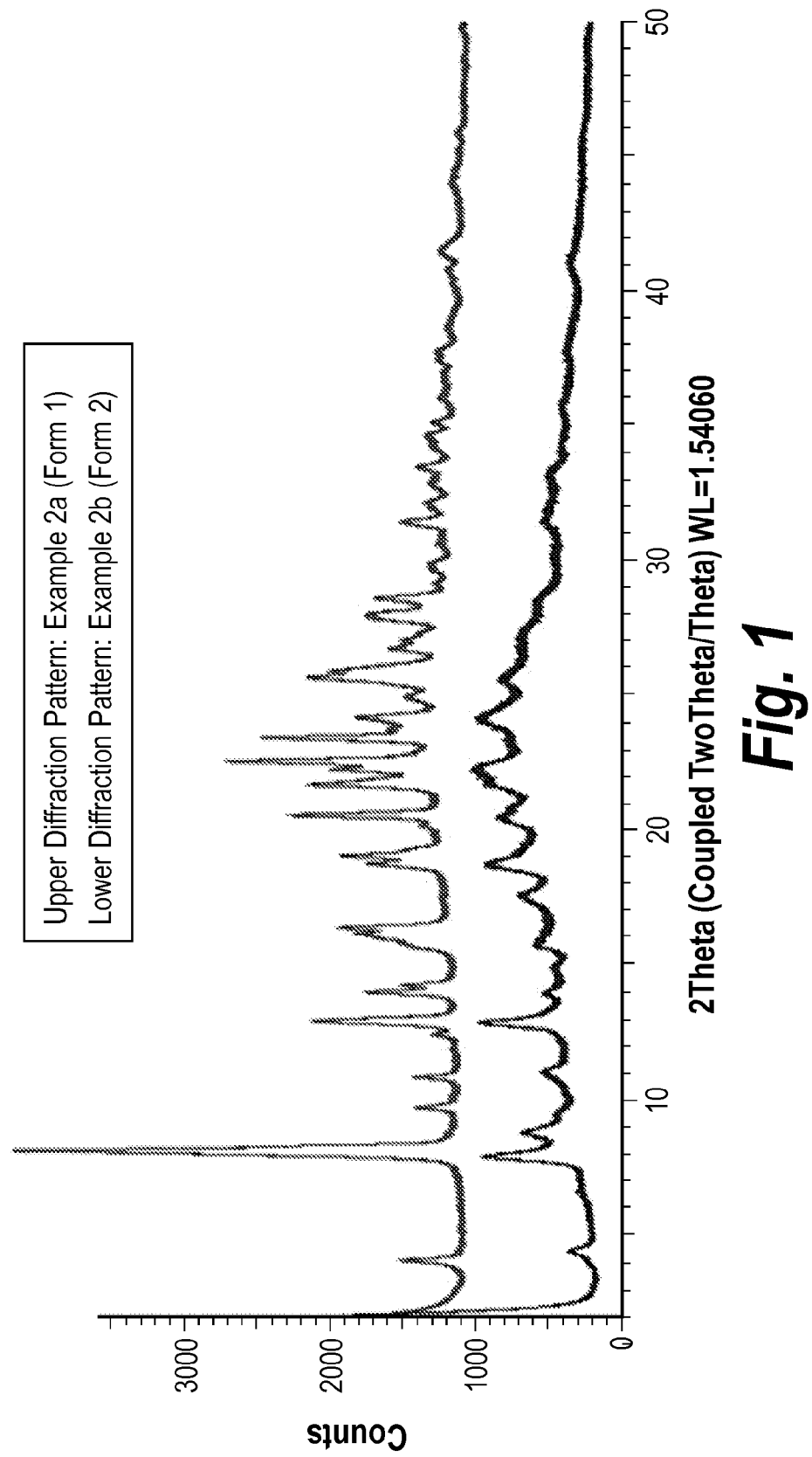
FIG. 1 depicts two X-ray powder diffraction patterns of novel solid forms ceftolozane sulfate. The upper pattern corresponds to the product of Example 2a. The lower pattern corresponds to the product of Example 2b.

Ceftolozane can be prepared as a pharmaceutically acceptable salt in one or more solid forms. Ceftolozane is also known as CXA-101; CAS registry number 689293-68-3; (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate, and 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate; 5-Thia-1-azabicyclo[4.2.0]oct-2-ene-2-carboxylic acid, 3-[[4-[[[(2-aminoethyl)amino]carbonyl]amino]-2,3-dihydro-3-imino-2-methyl-1H-pyrazol-1-yl]methyl]-7-[[(2Z)-2-(5-amino-1,2,4-thiadiazol-3-yl)-2-[(1-carboxy-1-methylethoxy)imino]acetyl]amino]-8-oxo-, (6R,7R)—; and (6R,7R)-3-[(5-amino-4-{[(2-aminoethyl)carbamoyl]amino}-1-methyl-1H-pyrazol-2-ium-2-yl)methyl]-7-({(2Z)-2-(5-amino-1,2,4-thiadiazol-3-yl)-2-[(1-carboxy-1-methylethoxy)imino]acetyl}amino)-8-oxo-5-thia-1-azabicyclo[4.2.0]oct-2-ene-2-carboxylate. Ceftolozane sulfate is an example of a pharmaceutically acceptable salt of ceftolozane. The structure of ceftolozane sulfate is shown below.

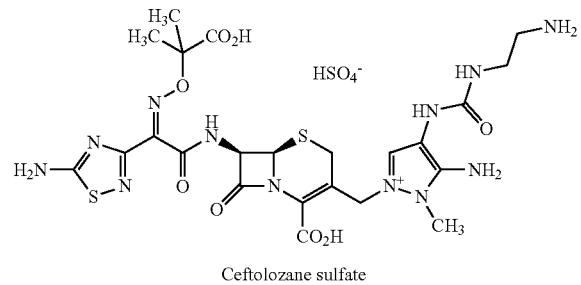 [SMILES: Cn1c(N)c(NC(=O)NCCN)c[n+]1CC1=C(C(=O)O)N2C(=O)[C@@H](NC(=O)/C(=N\OC(C)(C)C(=O)O)c3nsc(N)n3)[C@H]2SC1 ; "HSO4-"]

Ceftolozane sulfate

Ceftolozane sulfate is also referred to as: CAS registry number 936111-69-2; 1H-Pyrazolium, 5-amino-4-[[[(2-aminoethyl)amino]carbonyl]amino]-2-[[[(6R,7R)-7-[[(2Z)-2-(5-amino-1,2,4-thiadiazol-3-yl)-2-[(1-carboxy-1-methylethoxy)imino]acetyl]amino]-2-carboxy-8-oxo-5-thia-1-azabicyclo[4.2.0]oct-2-en-3-yl]methyl]-1-methyl-, sulfate (1:1); and 5-amino-4-{[(2-aminoethyl)carbamoyl]amino}-2-{[(6R,7R)-7-({(2Z)-2-(5-amino-1,2,4-thiadiazol-3-yl)-2-[(1-carboxy-1-methylethoxy)imino]acetyl}amino)-2-carboxy-8-oxo-5-thia-1-azabicyclo[4.2.0]oct-2-en-3-yl]methyl}-1-methyl-1H-pyrazolium monosulfate.

Ceftolozane sulfate can occur in an amorphous solid form or in a crystalline solid form or in mixtures of solid forms. Crystalline solid forms of ceftolozane can exist in one or more unique solid forms, which can additionally comprise one or more equivalents of water or solvent (i.e., hydrates or solvates, respectively).

As disclosed herein, crystalline ceftolozane sulfate precipitated or crystallized from isopropanol/water has significantly better stability in a solution comprising isopropanol compared to the stability in a solution comprising ethanol, as used to prepare crystalline ceftolozane sulfate precipitated from ethanol/water, as previously described in U.S. Pat. No. 7,129,232 (see Example 3). Moreover, the crystalline forms precipitated or crystallized from isopropanol/water have distinct characteristic XRPD peaks (see Examples 1 and 2, and Tables 4 and 6) that are not observed in previously disclosed crystal forms of ceftolozane described in U.S. Pat. No. 7,129,232. Accordingly, provided herein are novel crystalline ceftolozane sulfate solid forms, pharmaceutical compositions thereof, and methods of preparing those crystalline ceftolozane sulfate solid forms and methods of use thereof.

Novel ceftolozane solid forms can be obtained from aqueous solutions comprising ceftolozane and isopropyl alcohol (herein, also called IPA, or isopropanol). As described in Example 2a, ceftolozane sulfate in solid Form 1 can be obtained by forming a ceftolozane solution comprising a ceftolozane salt, a strong acid and IPA and maintaining the solution under conditions effective to form a ceftolozane wet cake containing Form 1 of the ceftolozane salt. Preferably, the ceftolozane solution is an aqueous solution comprising ceftolozane and the strong acid (e.g., sulfuric acid) in an amount providing least 1 molar equivalent of the strong acid to the molar quantity of ceftolozane in the solution. In certain examples, the Form 1 of ceftolozane is obtained from a ceftolozane solution that is polish filtered and the temperature is adjusted and maintained throughout the entire salt formation and isolation process. An aqueous sulfuric acid ($H_2SO_4$) solution can be charged to the batch. Optionally, this can be followed by seeding with ceftolozane sulfate crystal. The batch is aged, followed by the addition of IPA over a period of time. After the IPA addition, the batch is agitated for an additional period, and then filtered. The wet cake of ceftolozane sulfate is washed with a solution of IPA and water The ceftolozane solution is preferably maintained at a temperature effective to provide a desired purity and yield of the ceftolozane in solid Form 1, such as 8-12 degrees C. In addition to the temperature (e.g., 8-12 degrees C., preferably about 10 degrees C.), and amount of strong acid (e.g., sulfuric acid in an amount providing 1-3 molar equivalents, and preferably 2.45-2.55 molar equivalents, relative to the molar amount of ceftolozane), the concentration of ceftolozane before salt formation (e.g., 75-85 g/L), seed amount (e.g., 0.1-1 w/w %) and aging time after seeding (e.g., 2-4 hours) are also parameters that can be adjusted to obtain ceftolozane in Form 1 solid form. Particularly preferred processes for making Form 1 ceftolozane sulfate solid form include maintaining an aqueous solution of ceftolozane sulfate, isopropyl alcohol and sulfuric acid at a temperature of 8-12 degrees C. Table 1 provides the exemplary range of values for various process parameters for the manufacturing of solid forms of ceftolozane sulfate, along with preferred ranges and target (most preferred) values for each process parameter.

TABLE 1

Process Parameters for the Formation and Isolation of Ceftolozane Sulfate Solid Forms

| Process Parameter | Exemplary Range | Preferred Range | Target Value |
| --- | --- | --- | --- |
| Ceftolozane concentration after final nanofiltration (g/L) | 72 to 100 | 75 to 85 | 80 |
| Sulfuric acid (equiv) | 1.50 to 2.95 | 2.45 to 2.55 | 2.5 |
| Seed amount (w/w %) | 0.03 to 4.0 | 0.1 to 1.0 | 0.3 |
| Aging time, after seeding (h) | 1 to 5 | 2 to 4 | 3 |
| IPA amount (vol) | 20 to 40 | 29 to 31 | 30 |
| IPA addition time (h) | 0.5 to 8 | 6 to 7 | 6.5 |
| Aging time, after IPA addition (h) | 0 to 8 | 1 to 6 | 2 |
| Temperature (° C.) | 5 to 15 | 8 to 12 | 10 |
| 4:1 (v/v) IPA/water wash solution (vol) | ≥2 | ≥2 | 4 |

Solid forms of ceftolozane can be obtained by methods comprising the step of combining ceftolozane sulfate and a solvent, such that a solution comprising ceftolozane sulfate is formed, and such that crystalline ceftolozane sulfate precipitates from the solution. Crystalline ceftolozane sulfate solid forms can be obtained from methods that include the steps of: (1) combining ceftolozane sulfate and a solvent, such that a solution of ceftolozane sulfate is formed; and (2) combining an antisolvent with the solution, wherein the antisolvent is miscible with the solvent and wherein ceftolozane sulfate is partially or completely insoluble in the antisolvent, such that crystalline ceftolozane sulfate precipitates or crystallizes from the solution.

A ceftolozane sulfate composition can be obtained by a process comprising the steps of: (a) forming a solution comprising water, 72-100 g/L ceftolozane active and 1.5-2.95 molar equivalents of sulfuric acid to ceftolozane; (b) combining the solution from step (a) with 20-40 volumes of isopropyl alcohol added to the solution over 0.5-8 hours to obtain solid ceftolozane sulfate; and (c) isolating the solid ceftolozane sulfate from the solution. The temperature of the solution can be about 0-20 degrees C., preferably 8-12 degrees C. (e.g. 10 degrees C.). Optionally, the process can further include adding a ceftolozane sulfate seed crystal, preferably in an amount of 0.03-4.0% w/w and allowing the seed crystal to age in the solution for about 1-5 hours. Optionally, the process can include allowing the solution to age for up to about 8 hours after adding the isopropyl alcohol.

In another aspect, methods of making crystalline ceftolozane sulfate can include the steps of: (1) combining ceftolozane freebase (i.e., the non-salt form of ceftolozane having a net formal charge of zero) and a solvent, such that a solution of ceftolozane freebase is formed; (2) combining an acid with the solution of ceftolozane free base (e.g., in an amount providing a molar equivalent or excess of the acid to the ceftolozane free base, and/or an amount effective to adjust the pH of the ceftolozane solution to about 1.5-2.0); and (3) allowing the crystalline ceftolozane sulfate to precipitate or crystallize from solution. In addition, the method can include adding an antisolvent (preferably isopropyl alcohol) in an amount effective to provide a desired rate or extent of precipitation and/or crystallization of the ceftolozane in the solution. Accordingly, step (3) may further comprise combining an antisolvent with the solution, wherein the antisolvent is miscible with the solvent and wherein ceftolozane sulfate is partially or completely insoluble in the antisolvent, such that crystalline ceftolozane sulfate precipitates or crystallizes from the solution. In some embodiments, the temperature of the solution is adjusted to 0-20° C. In other embodiments, step (3) comprises the step of seeding the solution with one or more crystals of ceftolozane sulfate. In some embodiments, the volume of antisolvent that is added to the solution is 20-40 volumes relative to the ceftolozane. In some embodiments, the temperature of the solution formed in step (1) is adjusted to 0-20° C. before proceeding to step (2). In one embodiment, the method of making crystalline ceftolozane sulfate can also include the step of: (4) drying the precipitated or crystallized crystalline ceftolozane sulfate. Drying may comprise techniques including, but not limited to, air-drying, exposure to vacuum, exposure to a neutral gas (e.g., nitrogen) flow and heating.

In an alternative embodiment, the acid (e.g., sulfuric acid) may first be combined with the solvent, and the resulting mixture then combined with ceftolozane. Alternatively, ceftolozane and the acid (e.g., sulfuric acid) may first be combined, and the resulting mixture then combined with the solvent. In one embodiment, the antisolvent is added to the solution of ceftolozane sulfate or freebase. In another embodiment, the solution of ceftolozane sulfate or freebase is added to the antisolvent. In certain embodiments, the solvent is selected from the group consisting of water and sulfuric acid. In certain embodiments, the antisolvent is selected from the group consisting of alcohols, ethers, esters, ketones, nitriles, amides, nitroalkanes, nitroarenes, substituted or unsubstituted aromatic solvents, substituted or unsubstituted aliphatic solvents and mixtures thereof. In certain embodiments, the antisolvent is selected from the group consisting of acetone, acetonitrile, 1-butanol, cyclohexane, dichloromethane, diisopropyl ether, dimethylformamide, dimethylsulfoxide, 1,4-dioxane, ethanol, ethyl acetate, heptanes, methanol, isopropyl acetate, methyl ethyl ketone, methyl isobutyl ketone, N-methyl-2-pyrrolidinone, nitromethane, isopropanol, tert-butylmethyl ether, tetrahydrofuran, toluene and mixtures thereof. In a preferred embodiment, the solvent is water. In another preferred embodiment, the antisolvent is isopropanol.

Also provided herein is a method of making crystalline ceftolozane sulfate, comprising one or more steps selected from the group consisting of: (1) combining ceftolozane freebase, sulfuric acid and water, such that an aqueous solution of ceftolozane sulfate is formed; and (2) combining isopropanol with the aqueous solution, such that crystalline ceftolozane sulfate precipitates or crystallizes from the solution. In another aspect, provided herein is a method of making crystalline ceftolozane sulfate, comprising: (1) combining ceftolozane freebase, sulfuric acid, and a solvent/antisolvent mixture, such that a solution of ceftolozane sulfate is formed; and (2) combining an antisolvent with the solution, wherein the antisolvent is miscible with the solvent and wherein ceftolozane sulfate is partially or completely insoluble in the antisolvent, such that crystalline ceftolozane sulfate precipitates or crystallizes from the solution. In another aspect, provided herein is a method of making crystalline ceftolozane sulfate comprising the steps of: a) dissolving ceftolozane sulfate in water to obtain a first solution of ceftolozane sulfate; b) combining the first solution of ceftolozane sulfate with isopropanol to afford a second solution of ceftolozane sulfate; c) crystallizing ceftolozane sulfate from the second solution to obtain crystalline ceftolozane sulfate. In another aspect, provided herein is crystalline ceftolozane sulfate produced according to any one of the preceding methods. In another aspect, provided herein is crystalline ceftolozane sulfate obtainable by any one of the preceding methods. The processes and methods described herein may also further comprise adding one or more seed crystals of crystalline ceftolozane sulfate.

As used herein, the term "precipitate" refers to the formation of a solid substance from a solution containing the same substance. A substance which precipitates from solution may be amorphous or crystalline. Precipitation may occur under a variety of conditions known to those of skill in the art, including the treatment of a solution of a solute (e.g., solute A in solvent B) with an antisolvent (i.e., a solvent that is miscible with solvent B, but does not dissolve solute A). Non-limiting examples of solvent/antisolvent pairs include water/isopropanol.

The solid forms of ceftolozane can be identified by various analytical techniques, such as X-ray powder diffraction (XRPD). Solid forms of ceftolozane sulfate in solid Form 1 and a novel ceftolozane solid Form 2 of ceftolozane sulfate can both be identified by XRPD both having one or more shared characteristic diffractions at angles (2 theta±0.2) of 24.2 and 37.8. In addition, ceftolozane in both solid Form 1 and solid Form 2 can both produce the Raman spectra comprising one or more of the following peaks (+/−5 cm$^{-1}$) at about 597 cm$^{-1}$, 716 cm$^{-1}$, and 1329 cm$^{-1}$. A preferred ceftolozane composition can include ceftolozane in one or more solid forms (e.g., solid Form 1 and/or solid Form 2) characterized by XRPD pattern with diffractions at angles (2 theta±0.2) of 24.2 and 37.8, in addition to Raman spectra comprising one or more of the following peaks (+/−5 cm$^-$) at about 597 cm$^{-1}$, 716 cm$^{-1}$, and 1329 cm$^{-1}$. In addition, compositions comprising ceftolozane sulfate in solid Form 1 and/or solid Form 2 can be identified by XRPD patterns with diffractions at 2-theta values (2 theta±0.2) indicated in Table 4 (for Form 1) and/or Table 6 (for Form 2), respectively.

A novel ceftolozane solid Form 1 of ceftolozane sulfate can be identified by X-ray Powder Diffraction (XRPD), having one or more characteristic diffractions at angles (2 theta±0.2) of 12.4, 16.4, 22.6, 25.1, and 28.0. In addition, ceftolozane in solid Form 1 can produce the Raman spectra comprising one or more of the following peaks (+/−5 cm$^{-1}$) at 171 cm$^{-1}$, 743 cm$^{-1}$, 819 cm$^{-1}$, 1055 cm$^{-1}$, 2894 cm$^{-1}$, and 2976 cm$^{-1}$. In one embodiment, provided herein is crystalline ceftolozane sulfate Form 1 characterized by an X-ray powder diffraction pattern having peaks at substantially the same angles as the upper spectrum in FIG. 1. In another embodiment, the crystalline ceftolozane sulfate Form 1 is characterized by an X-ray powder diffraction pattern having one or more peaks at substantially the angles (2 theta±0.2) as Table 4.

A novel ceftolozane solid Form 2 of ceftolozane sulfate can be identified by X-ray Powder Diffraction (XRPD), having one or more characteristic diffractions at angles (2 theta±0.2) of 4.4, 8.8, 11.0, 14.9, and 17.7. In addition, ceftolozane in solid Form 1 can produce the Raman spectra comprising one or more of the following peaks (±5 cm$^{-1}$) at 151 cm$^{-1}$, 684 cm$^{-1}$, 802 cm$^{-1}$, 1174 cm$^{-1}$, and 2953 cm$^{-1}$. In one embodiment, the crystalline ceftolozane sulfate Form 2 is characterized by an X-ray powder diffraction pattern having characteristic peaks at substantially the same angles as the lower spectrum in FIG. 1. In another embodiment, the crystalline ceftolozane sulfate Form 2 is characterized by an X-ray powder diffraction pattern having one or more peaks at substantially the same angles (2 theta±0.2) as Table 6.

Crystalline forms of ceftolozane sulfate can also be characterized by their water content. In one embodiment, the crystalline ceftolozane sulfate comprises 11-27%, 12-26%, 13-25%, 14-24%, 15-23%, 16-22%, or 17-21% of water by weight. In a particular embodiment, the crystalline ceftolozane sulfate comprises 18-20% of water by weight. In another embodiment, the crystalline ceftolozane sulfate comprises about 26.3% by weight of water. In a particular embodiment, the crystalline ceftolozane sulfate is ceftolozane sulfate decahydrate.

Crystalline forms of ceftolozane sulfate can also be defined by their water content. In one embodiment, crystalline ceftolozane sulfate comprises 4-10%, 5-9%, or 6-8% of water by weight. Form 1 of ceftolozane sulfate can include about 18-20% water. Form 2 of ceftolozane sulfate can include less than about 11% water, and preferably about 5-11% water, and most preferably about 7-8% water.

In another embodiment, the crystalline ceftolozane sulfate comprises about 7% of water by weight. In a particular embodiment, the crystalline ceftolozane sulfate is ceftolozane sulfate trihydrate.

In some embodiments, crystalline ceftolozane sulfate can be characterized by Raman spectroscopy. In a particular embodiment, the crystalline ceftolozane sulfate in Form 1 has a Raman spectrum substantially in accordance with the upper spectrum shown in FIG. 2. In another particular embodiment, the crystalline ceftolozane sulfate in Form 1 has a Raman spectrum with one or more peaks at substantially the same positions ($\pm 5$ cm$^{-1}$) as shown in Table 5. Ceftolozane solid Form 1 can produce Raman shift peaks comprising one or more of the certain peaks not observed in Form 1, at about ($\pm 5$ cm$^{-1}$) 171 cm$^{-1}$, 743 cm$^{-1}$, 819 cm$^{-1}$, 1055 cm$^{-1}$, 2894 cm$^{-1}$, and 2976 cm$^{-1}$.

Figure 2:
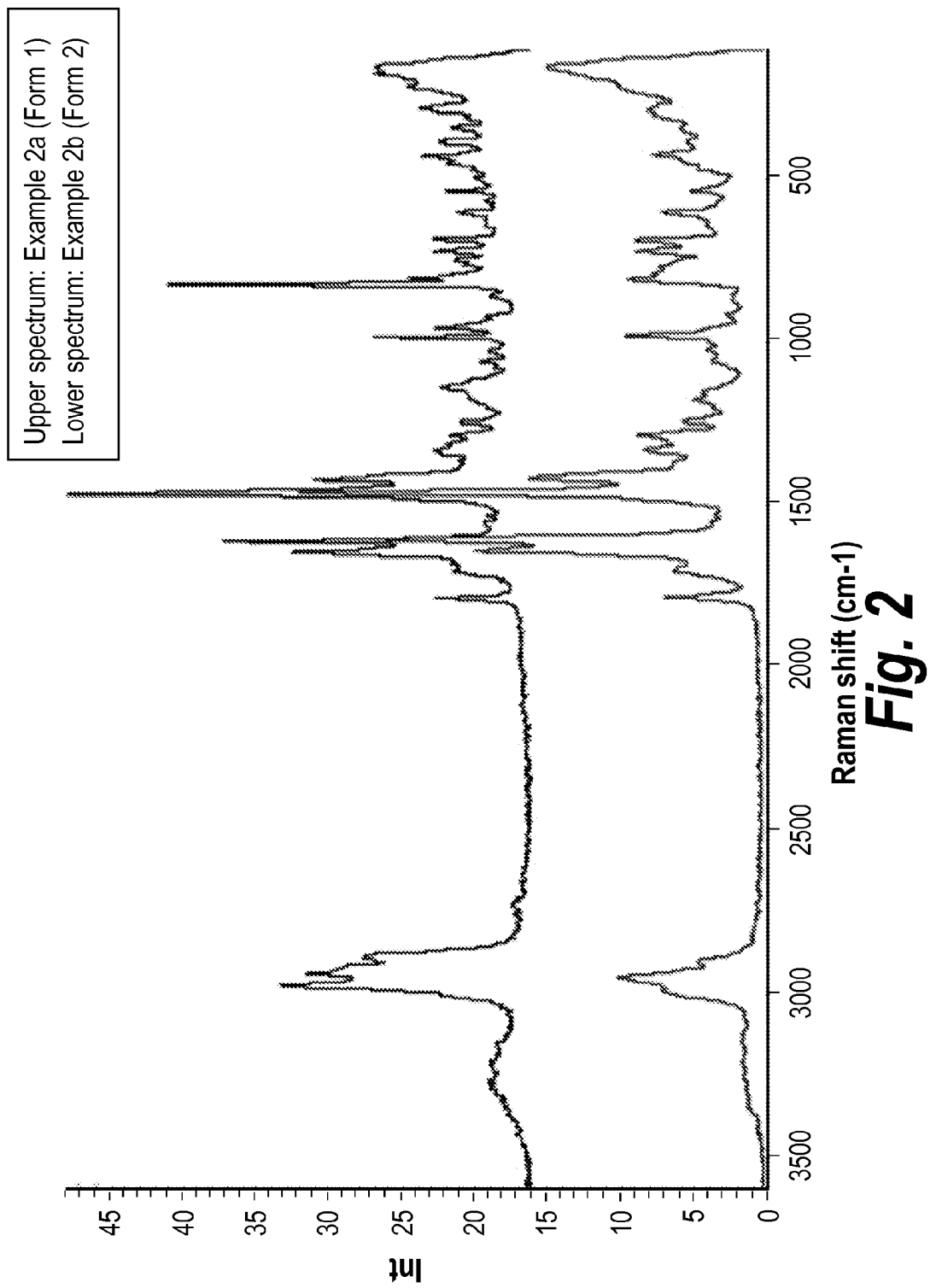
FIG. 2 depicts two Raman spectra of novel solid forms of ceftolozane sulfate. The upper pattern corresponds to the product of Example 2a. The lower pattern corresponds to the product of Example 2b.

In other embodiments, the crystalline ceftolozane sulfate in Form 2 has a Raman spectrum substantially in accordance with the lower spectrum shown in FIG. 2. In another particular embodiment, the crystalline ceftolozane sulfate in Form 2 has a Raman spectrum with one or more peaks at substantially the same positions ($\pm 5$ cm$^{-1}$) as shown in Table 7. Ceftolozane solid Form 2 can produce Raman shift peaks comprising one or more of the peaks at about ($\pm 5$ cm$^{-1}$) 151 cm$^{-1}$, 684 cm$^{-1}$, 802 cm$^{-1}$, 1174 cm$^{-1}$, and 2953 cm$^{-1}$.

Ceftolozane in solid Form 1 and solid Form 2 are both characterized by intense Raman shift peaks (+/-5 cm$^{-1}$) at about 597 cm$^{-1}$, 716 cm$^{-1}$, and 1329 cm$^{-1}$. In addition, ceftolozane solid Form 1 and Form 2 can produce Raman shift peaks comprising one or more of the following peaks at indicated in both Table 5 and 7 ($\pm 5$ cm$^{-1}$).

In another aspect, provided herein is a composition comprising amorphous and crystalline solid forms of ceftolozane sulfate. In one embodiment, the composition comprises crystalline ceftolozane sulfate and amorphous ceftolozane sulfate, wherein the amorphous ceftolozane sulfate is present in an amount selected from the following ranges: 90-99%, 80-89%, 70-79%, 60-69%, 50-59%, 40-49%, 30-39%, 20-29%, 10-19%, 1-9% and 0-0.99%.

In some embodiments, the crystalline ceftolozane sulfate is a hydrate. In one embodiment, the crystalline ceftolozane sulfate is ceftolozane sulfate decahydrate. In a particular embodiment, the crystalline ceftolozane sulfate comprises 5-amino-4-{-[(2-aminoethyl)carbamoyl]amino}-2-{[(6R,7R)-7-({(2Z)-2-(5-amino-1,2,4-thiadiazol-3-yl)-2-[(1-carboxy-1-methylethoxy)imino]acetyl}amino)-2-carboxy-8-oxo-5-thia-1-azabicyclo[4.2.0]oct-2-en-3-yl]methyl}-1-methyl-1H-pyrazolium monosulfate and water in a 1:10 molar ratio.

In another embodiment, the crystalline ceftolozane sulfate is ceftolozane sulfate trihydrate. In a particular embodiment, the ceftolozane sulfate comprises 5-amino-4-{-[(2-aminoethyl)carbamoyl]amino}-2-{[(6R,7R)-7-({(2Z)-2-(5-amino-1,2,4-thiadiazol-3-yl)-2-[(1-carboxy-1-methylethoxy)imino]acetyl}amino)-2-carboxy-8-oxo-5-thia-1-azabicyclo[4.2.0]oct-2-en-3-yl]methyl}-1-methyl-1H-pyrazolium monosulfate and water in a 1:3 molar ratio.

Compared with previous crystalline forms of ceftolozane sulfate, certain novel crystalline forms of ceftolozane sulfate have advantageous properties. For example, these crystalline forms were found to be more chemically stable, which can be beneficial to the preparation of various drug formulations.

A pharmaceutical composition can comprise, and/or be obtained from, the solid form of ceftolozane sulfate designated as ceftolozane sulfate Form 2 that produces an X-ray powder diffraction (XRPD) pattern having diffractions at angles (2 theta±0.2) of 4.4, 8.8, 11.0, 14.9 and 17.7. The ceftolozane sulfate can produce Raman shift peaks (+/-5 cm$^{-1}$) at about 151 cm$^{-1}$, 684 cm$^{-1}$, 802 cm$^{-1}$, 1174 cm$^{-1}$ and 2953 cm$^{-1}$.

A pharmaceutical composition can contain or be obtained from a solid form of ceftolozane characterized by one or more of the following: (a) the solid form of ceftolozane sulfate produces an XRPD pattern further comprising diffractions at angles (2 theta±0.2): 4.4, 8.8, 11.0, 14.9, and 17.7; (b) the solid form of ceftolozane sulfate of claim 1 that produces an XRPD pattern further comprising one or more additional diffractions at angles (2 theta±0.2) listed in Table 6; (c) the solid form of ceftolozane sulfate that produces Raman shift peaks at about ($\pm 5$ cm$^{-1}$) 151 cm$^{-1}$, 684 cm$^{-1}$, 802 cm$^{-1}$, 1174 cm$^{-1}$, and 2953 cm$^{-1}$; (d) the solid form of ceftolozane sulfate of claim 1 that produces one or more additional Raman shift peaks at values listed in Table 7; and any combination of one or more of characteristics (a)-(d).

A pharmaceutical composition can contain or be obtained from a lyophilized ceftolozane composition obtained by a process comprising the steps of: (a) combining ceftolozane sulfate in the solid form designated herein as ceftolozane sulfate in solid Form 2, with water, sodium chloride and L-arginine to form an aqueous solution; and (b) lyophilizing the aqueous solution to form the lyophilized composition comprising ceftolozane sulfate. The pharmaceutical composition obtained by such a method can include performing a lyophilization cycle characterized by one or more of the following characteristics: (a) not more than 150 mg ceftolozane free base/g bulk solution concentration, (b) no more than 3 cm fill depth, (c) freezing to at least –40° C. during the lyophilization cycle, (d) drying to no more than 40° C., and (e) single- or multi-step drying and setting chamber pressure during the start of primary drying at not more than 400µ bar.

A ceftolozane sulfate composition can be obtained by a process comprising the steps of: (a) forming a solution comprising water, 72-100 g/L ceftolozane active and 1.5-2.95 molar equivalents of sulfuric acid to ceftolozane; (b) combining the solution from step (a) with 20-40 volumes of isopropyl alcohol added to the solution over 0.5-8 hours to obtain solid ceftolozane sulfate; and (c) isolating the solid ceftolozane sulfate composition from the solution.

Pharmaceutical compositions comprising ceftolozane and tazobactam can be obtained by blending a first composition comprising a therapeutically effective amount of ceftolozane with a second composition comprising a therapeutically effective amount of tazobactam to form a blended pharmaceutical composition. The pharmaceutical composition can comprise ceftolozane or a therapeutically effective salt thereof and tazobactam or a pharmaceutically effective salt thereof in an amount providing about 500 mg of tazobactam active per 1,000 mg of ceftolozane active. The pharmaceutical antibiotic composition preferably includes ceftolozane and tazobactam in a 2:1 weight ratio of ceftolozane active to tazobactam active ("CXA-201"), which displays antibacterial activity, including antibiotic activity against infections caused by many Gram-negative pathogens such as *Pseudomonas aeruginosa* (*P. aeruginosa*). In particular, CXA-201 is a pharmaceutical composition useful for intravenous administration for the treatment of complicated intra-abdominal infections and/or complicated urinary tract infections, and is being evaluated for treatment of pneumonia.

Methods of treating an infection selected from the group consisting of: complicated intra-abdominal infection (cIAI), complicated urinary tract infection (cUTI), or hospital acquired/ventilator-associated bacterial pneumonia (HABP/VABP) are also provided herein. These methods can include administering to a patient an injectable pharmaceutical composition comprising ceftolozane in an injectable preparation prepared from a lyophilized composition obtained by a process comprising the steps of: (a) combining the ceftolozane sulfate in a solid form that produces an X-ray powder diffraction (XRPD) pattern having diffractions at angles (2 theta±0.2) of 4.4, 8.8. 11.0, 14.9, and 17.7 with water to form an aqueous solution; and (b) lyophilizing the aqueous solution to form the lyophilized ceftolozane composition comprising ceftolozane sulfate.

Pharmaceutical compositions can be obtained by combining tazobactam (or a pharmaceutically acceptable salt thereof) in one or more solid forms with a ceftolozane composition comprising ceftolozane in one or more salts and/or solid forms. The ceftolozane in the pharmaceutical composition can be ceftolozane sulfate in one or more solid forms disclosed herein, including amorphous, Form 1, Form 2 and/or combinations thereof. The ceftolozane in the pharmaceutical composition can be obtained by a process comprising lyophilizing a solution of ceftolozane sulfate in solid Form 1, solid Form 2 and/or combinations thereof. For example, the ceftolozane in the pharmaceutical composition can be prepared in the absence of tazobactam by forming an aqueous solution comprising ceftolozane sulfate in solid Form 1, solid Form 2 and/or combinations thereof and other components including excipients, stabilizers, pH adjusting additives (e.g., buffers) and the like. Non-limiting examples of these additives include sodium chloride, citric acid and L-arginine. For example, the use of sodium chloride results in greater stability; L-arginine is used to adjust the aqueous solution to a pH of 5-7 (e.g., to pH 6-7) and to increase the solubility of ceftolozane; and citric acid is used to prevent discoloration of the product, due to its ability to chelate metal ions. In one embodiment, the pH of the first aqueous solution is suitable for making an injectable product (e.g., a pH range of 5-7, including 6-7). Preferably, the first aqueous solution comprises about 125 mg-500 mg of a ceftolozane stabilizing agent (such as sodium chloride) per 1,000 mg of ceftolozane active. The ceftolozane can be included as an amount of ceftolozane sulfate of formula (I) containing at least about 1,000 mg ceftolozane active. The aqueous solution comprising ceftolozane (e.g., ceftolozane sulfate in Form 2, and/or other solid forms disclosed herein) is then lyophilized to form a first lyophilized ceftolozane composition, which is combined with tazobactam, e.g., the lyophilized tazobactam (e.g., lyophilized tazobactam sodium) or crystalline tazobactam The pharmaceutical composition can be obtained by combining the ceftolozane composition with a (second) tazobactam composition (e.g., preferably, but not necessarily, prepared in the absence of ceftolozane) by forming a second solution comprising tazobactam. The tazobactam can be included in an amount providing about 500 mg of tazobactam active per 1,000 mg ceftolozane active (i.e., a 1:2 weight ratio of tazobactam active to ceftolozane active). Tazobactam is a beta-lactamase inhibitor in its free acid form. Unless otherwise indicated, tazobactam can be a free acid, a sodium salt, an arginine salt, or a hydrate or solvate thereof. In one embodiment, the tazobactam in the (second) tazobactam composition is tazobactam acid and the second composition further comprises sodium bicarbonate or sodium hydroxide. Lyophilizing tazobactam in the presence of sodium bicarbonate or sodium hydroxide forms a lyophilized tazobactam sodium, which can then be further blended with the (first) lyophilized ceftolozane composition.

Pharmaceutical compositions can be obtained by lyophilization (e.g., lyophilizing an aqueous ceftolozane solution obtained by dissolving ceftolozane in Form 2 and/or Form 1 with other components such as a stabilizing agent, a chelating agent and/or an alkalizing agent). Specific methods of lyophilization are described in Remington's Pharmaceutical Sciences, Chapter 84, page 1565, Eighteenth Edition, A. R. Gennaro, (Mack Publishing Co., Easton, Pa., 1990).

Pharmaceutical compositions comprising ceftolozane and tazobactam can be formulated to treat infections by parenteral administration (including subcutaneous, intramuscular, and intravenous) administration. Pharmaceutical compositions may additionally comprise excipients, stabilizers, pH adjusting additives (e.g., buffers) and the like. Non-limiting examples of these additives include sodium chloride, citric acid and L-arginine. For example, the use of sodium chloride results in greater stability; L-arginine is used to adjust pH and to increase the solubility of ceftolozane; and citric acid is used to prevent discoloration of the product, due to its ability to chelate metal ions. In one particular embodiment, the pharmaceutical compositions described herein are formulated for administration by intravenous injection or infusion.

The pharmaceutical antibiotic compositions can be provided in a unit dosage form container (e.g., in a vial or bag, or the like). The unit dosage form can be dissolved with a pharmaceutically acceptable carrier, and then intravenously administered. The unit dosage form comprises 1000 mg of ceftolozane active and 500 mg tazobactam, typically 1000 mg ceftolozane active as ceftolozane sulfate and 500 mg of tazobactam active as tazobactam sodium, argininate or free acid. The unit dosage forms are commonly stored in vials.

In one aspect, provided herein is a unit dosage form container (e.g., a bag, vial or the like) containing a unit dosage form of a pharmaceutical composition formulated for parenteral administration for the treatment of complicated intra-abdominal infections, the pharmaceutical composition comprising a therapeutically effective amount of ceftolozane sulfate and tazobactam in a ratio of 1,000 mg ceftolozane active per 500 mg of tazobactam active, the pharmaceutical composition obtained by a process comprising the steps of:

a. lyophilizing a first aqueous solution in the absence of tazobactam, the first aqueous solution comprising ceftolozane sulfate, 125 mg to 500 mg of sodium chloride per 1,000 mg of ceftolozane active, L-arginine and/or citric acid in an amount effective to adjust the pH of the first aqueous solution to 5-7 (e.g., 6-7) prior to lyophilization to obtain a first lyophilized ceftolozane composition, b. lyophilizing a second solution in the absence of ceftolozane, the second solution comprising tazobactam being lyophilized to form a second lyophilized tazobactam composition; and c. blending the first lyophilized ceftolozane composition and the second lyophilized tazobactam composition to obtain a blended pharmaceutical composition in the unit dosage form.

In one embodiment of the unit dosage form container, the tazobactam in the second solution is tazobactam acid, and wherein the tazobactam acid in the second solution is lyophilized in the presence of sodium bicarbonate or sodium hydroxide, thereby forming lyophilized tazobactam sodium in the second lyophilized tazobactam composition.

The pharmaceutical compositions provided herein comprising ceftolozane sulfate and tazobactam in a ratio of 1,000 mg ceftolozane active per 500 mg of tazobactam active, can be obtained by a process comprising the steps of:

a. lyophilizing a first aqueous solution in the absence of tazobactam, the first aqueous solution comprising ceftolozane sulfate at a pH of 5-7 (e.g, 6-7) prior to lyophilization to obtain a first lyophilized ceftolozane composition, b. blending the first lyophilized ceftolozane composition with tazobactam to obtain an antibacterial composition.

As provided herein, ceftolozane can be stabilized in a pharmaceutical composition comprising ceftolozane and a stabilizing effective amount of a stabilizing agent selected from the group consisting of: sodium chloride, dextran 40, lactose, maltose, trehalose and sucrose. The pharmaceutical compositions provided herein are based in part on the surprising discovery that ceftolozane pharmaceutical compositions comprising these stabilizing agents demonstrate improved ceftolozane residual rates (e.g., % ceftolozane remaining after 3 days at 70 degrees C. as measured by HPLC) and/or chemical stability (e.g., lower reduction in ceftolozane purity measured by HPLC after 7 days at 60 degrees C. in a stability test) compared control samples comprising ceftolozane without a stabilizing agent.

Accordingly, preferred pharmaceutical antibiotic compositions can include ceftolozane sulfate and a stabilizing agent (e.g., 300 to 500 mg of a stabilizing agent per 1,000 mg ceftolozane active) in a lyophilized unit dosage form (e.g., powder in a container). The unit dosage form can be dissolved with a pharmaceutically acceptable carrier (e.g., 0.9% sodium chloride aqueous isotonic saline and/or water for injection), and then intravenously administered. In certain ceftolozane compositions, the stabilizing agent can be selected from the group consisting of: sodium chloride, lactose, maltose and dextran 40, and/or selected from the group consisting of: sodium chloride, trehalose and sucrose.

Ceftolozane pharmaceutical compositions comprising 125 to 500 mg (e.g., 480 to 500 mg) of sodium chloride per 1000 mg of ceftolozane active demonstrate improved ceftolozane purity and chemical stability compared to pharmaceutical compositions comprising ceftolozane with comparatively less sodium chloride. The disclosed ceftolozane pharmaceutical compositions comprise a stabilizing amount of sodium chloride (e.g., 125 to 500 mg of sodium chloride [more specifically, 480 to 500 mg] per 1000 mg of ceftolozane active). Certain preferred compositions demonstrate improved ceftolozane purity and chemical stability compared with pharmaceutical compositions comprising ceftolozane with comparatively less sodium chloride. For example, the disclosed pharmaceutical compositions typically comprise less than about 4% total impurity after being stored for seven days at 60 degrees C., as determined by HPLC. Alternatively, the disclosed pharmaceutical compositions comprise less than about 2% of the impurity represented by Peak 1 after being stored for seven days at 60° C., as determined by HPLC (refer to the HPLC method described in Table 10), where Peak 1 has a retention time relative to ceftolozane of approximately 0.15.

Another embodiment of the invention is a container containing a unit dosage form of a pharmaceutical composition formulated for parenteral administration for the treatment of complicated intra-abdominal infections or complicated urinary tract infections. The container can be obtained by a process comprising the steps of: a) lyophilizing an aqueous solution comprising 189 mg sodium from sodium chloride per 1000 mg ceftolozane active in the form of ceftolozane sulfate and further comprising citric acid, and L-arginine to obtain a lyophilized ceftolozane composition; and b) filling a sufficient quantity of the lyophilized composition into a container to obtain a unit dosage form comprising a ceftolozane stabilizing effective amount of sodium from sodium chloride (e.g., 125-500 mg sodium chloride per 1 g ceftolozane active) and 1,000 mg of ceftolozane active in the form of ceftolozane sulfate. In one aspect, the pH of the aqueous solution is 6.0 to 7.0. In another aspect the pharmaceutical composition is formulated for parenteral administration by reconstituting the pharmaceutical composition in the container (e.g., with 10 mL of diluent such as water for injection or isotonic saline) followed by addition of the reconstituted pharmaceutical composition to a carrier for injection (e.g., about 100 mL of isotonic saline or other pharmaceutically acceptable carrier for intravenous administration). Optionally, the container is also filled with tazobactam (e.g., a lyophilized tazobactam such as tazobactam sodium). In yet another aspect, the pharmaceutical composition is a liquid composition comprising 487 mg sodium chloride per 1,000 mg of ceftolozane active and tazobactam in an amount providing about 500 mg tazobactam acid equivalent per 1,000 mg of ceftolozane active, formulated for parenteral administration and the pH of the aqueous solution is 5.0 to 7.0 and preferably about 6.0 to 7.0.

The pharmaceutical composition in the container can also be a Ceftolozane/Tazobactam for Injection Drug Product, 1000 mg/500 mg. It is presented as a combination of two sterile active powders in a single container intended for reconstitution and intravenous infusion. In one embodiment, the drug product is prepared by converting ceftolozane sulfate to a sterile composition as a powder with excipients citric acid, sodium chloride and L-arginine. This is can done by lyophilization, as described herein. Tazobactam sodium drug substance can be presented as a sterile powder without any excipients. The tazobactam sodium drug substance can be lyophilized, spray dried or provided as a crystalline material. The drug product is then prepared by aseptically filling the two powders (e.g., the two separately lyophilized drug powders) sequentially into a single container.

In an embodiment, the container of ceftolozane/tazobactam for injection contains approximately 2255 mg ceftolozane sterile composition powder that contains 1147 mg ceftolozane sulfate, which is equivalent to 1000 mg ceftolozane free base, as well as approximately 537 mg tazobactam sodium sterile drug substance, equivalent to 500 mg tazobactam free acid. At the time of administration, the container is reconstituted with 10 mL vehicle, sterile 5% Dextrose Injection USP, Water for Injection or 0.9% Sodium Chloride Injection USP, then the container contents further diluted in an infusion bag of 0.9% Sodium Chloride Injection USP or 5% Dextrose Injection USP, for administration.

Ceftolozane-containing pharmaceutically compositions can also include an amount of tazobactam in a pharmaceutically acceptable form providing 500 mg of tazobactam acid per 1,000 mg of ceftolozane active as a composition formulated for injection, or for reconstitution prior to parenteral administration. In one product presentation, ceftolozane/tazobactam can be provided in a single container comprising ceftolozane sulfate and tazobactam sodium, administered by reconstituting a container-unit dosage form container of solid ceftolozane/tazobactam to form a reconstituted injectable formulation. In one presentation (e.g., for treatment of certain urinary tract infections and/or certain intra-abdominal infections), each unit dosage form container of CXA-201 can contain 1000 mg of ceftolozane active (free base equivalent weight, e.g., provided as a pharmaceutically acceptable salt such as ceftolozane sulfate) and sterile tazobactam sodium at a quantity equivalent of 500 mg of tazobactam free acid, in a solid form. In another presentation (e.g., for treatment of hospital acquired/ventilator-associated bacterial pneumonia (HABP/VABP)), a ceftolozane/tazobactam product can include a unit dosage form container providing 2,000 mg of ceftolozane active (e.g., as an equivalent amount of ceftolozane sulfate) and 1,000 mg of tazobactam acid (e.g., as an equivalent amount of tazobactam sodium). Ceftolozane/tazobactam compositions display potent antibacterial activity against various gram-negative infections such as, for example, complicated intra-abdominal infection (cIAI), complicated urinary tract infection (cUTI), or hospital acquired/ventilator-associated bacterial pneumonia (HABP/VABP).

Ceftolozane/tazobactam can be used for treating an infection selected from the group consisting of: urinary tract infections, and intra-abdominal infections. The methods of treatment can include intravenously administering to a patient in need thereof a therapeutically effective amount of a pharmaceutical composition comprising ceftolozane sulfate and an amount of tazobactam providing about 500 mg of tazobactam active per 1,000 mg of ceftolozane active, the ceftolozane sulfate in the pharmaceutical composition obtained from a ceftolozane sulfate solid form obtained by a process comprising the steps of: (a) combining the ceftolozane sulfate in a solid form, designated as ceftolozane sulfate Form 2, with water, sodium chloride and L-arginine to form an aqueous solution; (b) lyophilizing the aqueous solution to form the lyophilized ceftolozane composition comprising ceftolozane sulfate; (c) combining the lyophilized ceftolozane composition with tazobactam to obtain the pharmaceutical composition; (d) reconstituting the pharmaceutical composition in a pharmaceutically acceptable diluent; and (e) intravenously administering the reconstituted pharmaceutical composition to the patient.

EXAMPLES

Instrumentation and Methods

Other than Comparative Example 1, and unless otherwise indicated, the following instrumentation and methods were used in the working Examples described herein. Comparative Example 1 is reported in U.S. Pat. No. 7,232,129.

X-ray Powder Diffraction (XRPD)

High Resolution X-ray Powder Diffraction experiments (Bruker, AXS D8 Advance) were performed on a Bruker D8 diffractometer using Cu Kα radiation (40 kV, 40 mA), θ-2θ goniometer, and primary & secondary soller slits)(2.5°, a Ge monochromator and Lynxeye detector (opening angle of 2.948°). Certified Corundum standard (NIST 1976) was used to check the performance of the instrument. Data collection was performed by the Diffrac.Suite Measurement Center v2.2.47.1 and the data was analyzed and presented using Diffrac.EVA v2.0 or v3.0.

Samples were tested under ambient conditions. Approximately 500 mg of each sample was grinded for 3 minutes in a mortar and pestle. The sample was prepared by back-loading the triturated material into the sample holder and supporting it with a zero background silicon wafer. Once tightly packed, a flat surface was formed. When the sample was carefully flipped over, the appearance of the API in the sample holder appeared very similar to the appearance of the Corundum sample for NIST used to verify the performance of the instrument. The scan type of coupled TwoTheta/Theta was used for the data collection. The angular range was 2 to 50° 2θ, and the step size was 0.001° 2θ. Collection Time was 1 s for the each step. The geniometer radius was set at 280 mm. Sample rotation speed was 15 rpm, and the slit size was 0.1 mm.

Thermal Analysis

Thermo Gravimetric Analysis (TGA) experiments were performed on a TA Instruments Discovery Series TGA. The calibration for temperature was carried out using certified indium. Typically, 3-15 mg of a sample was flattened into sealed aluminum pans. Data was acquired for samples with and without a pinhole. For samples with a pinhole, once crimped and sealed, the auto-sampler punched the lid of the sample with its internal puncher right before analysis of the sample. Samples were heated at 20° C./min from 30° C. to 400° C. Dry nitrogen was purged into the system during the experiment at a rate of 50 ml/min. The software used to control the instrument was TRIOS Explorer Software v5.3.0.75. TRIOS software v2.40.1838 or v2.04.04563 was used for data analysis.

Differential Scanning calorimetry (DSC) experiments were performed on a TA Instruments Q2000 was used for collecting DSC data. The calibration for thermal capacity was carried out using sapphire and the calibration for energy and temperature was carried out using certified indium. Typically, 3-10 mg of a sample is flattened into sealed aluminum hermetic pans and the weight accurately recorded. Data was acquired for samples with a pinhole in the lid. Samples were heated at 10° C./min from 25° C. to 350° C. Dry nitrogen was purged into the system during the experiment at a rate of 50 ml/min. The software used to control the instrument is the Advantage for Q Series v2.9.0.396 and the Thermal Advantage v5.4.0. Data was analyzed using the Universal Analysis v4.5A software.

Gravimetric Dynamic Vapour Sorption

Gravimetric dynamic vapor sorption data (FIG. 5) was obtained using a SMS DVS Intrinsic moisture sorption analyser, controlled by DVS Intrinsic Control software v1.0.0.30. The sample temperature was maintained at 25° C. by the instrument controls. The humidity was controlled by mixing streams of dry and wet nitrogen. The relative humidity was measured by a calibrated Rotronic probe, located near the sample. The weight change of the sample as a function of % RH was constantly monitored by the microbalance (accuracy ±0.005 mg). Approximately 40 mg of sample was placed in a tared mesh stainless basket under ambient conditions. Weight reference was established at the start of an experiment. Moisture sorption isotherm parameters were described as below:

TABLE 2

| Parameters | Values |
| --- | --- |
| Scan 1 Adsorption | 40%-90% |
| Scan 2 Desorption/Adsorption | 90%-0%/0%-40% |
| Interval (RH step increments) | 10% |
| Number of Scans | 4 (double cycle) |
| Flow rate for dry and wet $N_2$ | 200 ml/min |
| Temperature | 25° C. |
| Temperature Stabiiity | 0.2° C./min |
| Time out | 6 hrs |

Data analysis was undertaken in Microsoft Excel using DVS Analysis Suite v6.0. The sample was recovered after completion of the isotherm experiment for solid state characterization.

Spectroscopy Measurement

Raman spectra were acquired on a Fourier transform Raman 960 spectrometer (Thermo Nicolet) equipped with a germanium (Ge) detector. Wavelength verification was performed using sulfur and cyclohexane. Each sample was packed into a pellet and placed into a pellet holder accessory for analysis. Approximately 0.505 W of Nd:YVO$_4$ laser power (1064 nm excitation wavelength) was used to irradiate each sample. Peak lists were generated using OMNIC software v7.2a.

(Comparative) Example 1

Solid Form Disclosed in U.S. Pat. No. 7,129,232

A solution of 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylate (36 g) in water was purified by preparative HPLC utilizing ODS column. The eluate containing a desired product was concentrated to about 1.5 L in vacuo. The concentrate was adjusted to about pH 1 with concentrated hydrochloric acid and chromatographed on Diaion® HP-20 (6 L) eluting with 20% aqueous 2-propanol. The eluate was concentrated to about 800 ml in vacuo, and 2M sulfuric acid (17 ml) was added. The resulting solution was lyophilized to give a sulfuric acid salt as an amorphous powder (23.6 g).

The powder was dissolved in water (71 ml) and ethanol (57 ml). After addition of seed crystals (310 mg), which resulted in the precipitation of white solid, the mixture was stirred for 1 hour. A mixture of ethanol (47 ml) and water (37 ml) was added over 30 minutes, and ethanol (33 ml) was added over 20 minutes. Then the slurry was stirred for an additional 1.5 hour. The precipitate was collected by filtration, washed with ethanol/water (60 ml/20 ml) and ethanol (60 ml) and dried to give 7β-[(Z)-2-(5-amino-1,2,4-thiadiazol-3-yl)-2-(1-carboxy-1-methylethoxyimino)acetamido]-3-{3-amino-4-[3-(2-aminoethyl)ureido]-2-methyl-1-pyrazolio}methyl-3-cephem-4-carboxylic acid hydrogen sulfate as crystals (17.3 g).

IR(KBr) 3353, 3183, 1778, 1652, 1558, 1403, 1321, 1143, 1118, 997, 619 cm$^{-1}$ $^1$H-NMR (D$_2$O) δ 1.61 (6H, s), 3.10-3.55 (6H, m), 3.71 (3H, s), 5.02 and 5.23 (2H, ABq, J=16.7 Hz), 5.25 (1H, d, J=4.9 Hz), 5.87 (1H, d, J=4.9 Hz), 7.91 (1H, s)

ESI-MS: m/z=667 (M+H$^+$)

TABLE 3

X-ray powder diffraction analysis (by Rigaku X-ray Diffraction system MultiFlex)

| 2θ | intensity |
| --- | --- |
| 8.0 | 1286 |
| 12.7 | 586 |
| 13.8 | 423 |
| 16.1 | 618 |
| 18.9 | 520 |
| 20.4 | 748 |
| 21.5 | 667 |
| 22.4 | 1058 |
| 23.3 | 944 |
| 24.0 | 618 |
| 25.5 | 813 |
| 26.7 | 472 |
| 27.9 | 537 |
| 28.5 | 455 |
| 31.3 | 390 |

X-ray: Cu/40 kV/30 mA

Example 2a

Novel Solid Form of Ceftolozane Sulfate

To obtain ceftolozane sulfate in Form 1: ceftolozane (1 molar equivalent) was dissolved in water to afford a solution at a concentration of 80 g/L. An aqueous solution of sulfuric acid (20-98%, 2.5 molar equivalents) was added at 0-20° C. The resulting solution was seeded with ceftolozane sulfate (0.01 to 0.05% by weight relative to active ceftolozane) and allowed to stir for 1-3 hours at 0-20° C. A precipitation was observed. Isopropanol (20-40 volumes relative to active ceftolozane) was added to result in a slurry at 0-20° C. After filtration, crystalline ceftolozane sulfate was obtained. The X-ray powder diffraction pattern of the crystalline ceftolozane sulfate Form 1 is depicted in FIG. 1 (upper diffraction pattern), and the corresponding data is summarized in Table 4. The Raman spectrum of the crystalline ceftolozane sulfate Form 1 is depicted in FIG. 2 (upper spectrum), and the corresponding data is summarized in Table 5.

TABLE 4

X-ray Powder Diffraction Patterns for Ceftolozane Sulfate Form 1 (Example 2a) Ceftolozane Sulfate Form 1

| Angle [°2θ] | Intensity [cts] |
| --- | --- |
| 4.061 | 629 |
| 8.126 | 3275 |
| 9.748 | 511 |
| 10.865 | 521 |
| 12.435 | 399 |
| 12.954 | 1225 |
| 14.016 | 867 |
| 14.284 | 613 |
| 16.177 | 937 |
| 16.413 | 1048 |
| 18.796 | 847 |
| 19.094 | 1024 |
| 20.200 | 484 |
| 20.596 | 1393 |
| 21.732 | 1260 |
| 22.278 | 1098 |
| 22.603 | 1816 |
| 23.490 | 1554 |
| 23.777 | 720 |
| 24.268 | 913 |
| 25.059 | 590 |
| 25.678 | 1261 |
| 25.929 | 1107 |
| 26.746 | 701 |
| 27.102 | 619 |
| 28.017 | 854 |
| 28.668 | 792 |
| 29.265 | 390 |
| 29.972 | 428 |
| 31.513 | 612 |
| 32.917 | 423 |
| 33.526 | 512 |
| 34.773 | 431 |
| 35.191 | 408 |
| 36.111 | 361 |
| 37.504 | 366 |
| 37.723 | 373 |
| 38.778 | 312 |
| 40.860 | 299 |
| 41.631 | 350 |
| 44.084 | 281 |
| 45.997 | 235 |

TABLE 5

Raman peaklist for ceftolozane sulfate Form 1 (Example 2a) Ceftolozane Sulfate Form 1

| Position (cm$^{-1}$) | Intensity (Counts) |
| --- | --- |
| 170.5 | 5.402 |
| 276.5 | 3.852 |
| 336.1 | 2.78 |
| 381.2 | 3.172 |
| 424 | 3.787 |
| 530.9 | 2.974 |
| 596.7 | 2.607 |
| 680.9 | 3.385 |

TABLE 5-continued

Raman peaklist for ceftolozane sulfate Form 1 (Example 2a)
Ceftolozane Sulfate Form 1

| Position (cm$^{-1}$) | Intensity (Counts) |
|---|---|
| 716.2 | 3.408 |
| 742.8 | 2.64 |
| 798.8 | 4.282 |
| 818.7 | 12.666 |
| 951.9 | 3.307 |
| 980.9 | 5.46 |
| 1055.3 | 1.794 |
| 1135.1 | 3.121 |
| 1242 | 2.471 |
| 1285 | 2.835 |
| 1328.5 | 3.402 |
| 1418.7 | 7.494 |
| 1464.1 | 15.996 |
| 1607.7 | 10.642 |
| 1642.3 | 8.252 |
| 1786 | 3.322 |
| 2893.8 | 5.886 |
| 2940.8 | 7.789 |
| 2976.1 | 8.658 |
| 3265.8 | 1.5 |

Example 2b

Novel Solid Form of Ceftolozane Sulfate

To obtain ceftolozane sulfate in Form 2: The ceftolozane sulfate obtained as Form 1 in Example 2a was dried under vacuum and nitrogen bleed at 20-25° C. for 24-48 hours to afford crystalline ceftolozane sulfate (vacuum-dried). The X-ray powder diffraction pattern of the crystalline ceftolozane sulfate Form 2 is depicted in FIG. 1 (lower diffraction pattern), and the corresponding data is summarized in the Table 6.

TABLE 6

X-Ray Powder Diffraction Pattern of Ceftolozane
Sulfate Form 2 (Example 2b)
Ceftolozane Sulfate Form 2

| Angle [°2θ] | Intensity [cts] |
|---|---|
| 4.400 | 348 |
| 7.900 | 950 |
| 8.827 | 700 |
| 9.381 | 466 |
| 11.000 | 536 |
| 12.861 | 981 |
| 13.980 | 534 |
| 14.913 | 479 |
| 15.753 | 610 |
| 17.673 | 711 |
| 18.749 | 923 |
| 20.488 | 858 |
| 21.692 | 924 |
| 22.178 | 1020 |
| 24.235 | 1000 |
| 25.678 | 842 |
| 27.180 | 708 |
| 28.593 | 587 |
| 31.482 | 546 |
| 33.277 | 508 |
| 34.397 | 438 |
| 35.789 | 428 |
| 37.767 | 403 |

The Raman spectrum of the crystalline ceftolozane sulfate Form 2 is depicted in FIG. 2 (lower spectrum), and the corresponding data is summarized in Table 7. Table 7 lists the Raman shift peaks for ceftolozane sulfate in solid Form 2.

TABLE 7

Raman peak list for ceftolozane sulfate
form 2 (Example 2b)
Ceftolozane Sulfate Form 2

| Position (cm$^{-1}$) | Intensity (Counts) |
|---|---|
| 151 | 11.618 |
| 282 | 6.341 |
| 418.1 | 6.139 |
| 530.2 | 4.005 |
| 596.8 | 5.656 |
| 683.7 | 7.226 |
| 716.2 | 6.968 |
| 802.3 | 7.45 |
| 976.9 | 7.505 |
| 1174.2 | 3.974 |
| 1237 | 4.582 |
| 1282.1 | 6.944 |
| 1328.1 | 6.577 |
| 1414.3 | 12.424 |
| 1458.5 | 25.508 |
| 1602.2 | 20.204 |
| 1637.5 | 15.561 |
| 1782 | 5.388 |
| 2952.8 | 7.588 |

The moisture sorption/desorption property of crystalline cefolozane sulfate form 2 is depicted in FIG. 5. A reversible hysteresis associated with around 23% w/w water between 0% and 90% relative humidity (RH) was observed. The DVS isotherm in FIG. 5 is consistent with the presence of two crystalline forms that can be interconverted as function of relative humidity. The presence of ceftolozane sulfate solid Form 1 and ceftolozane sulfate solid Form 2 in the sample tested to obtain the DVS isotherm in FIG. 5 was confirmed by a variable humidity XRPD (VH-XRPD) measurement, based on the XRPD diffraction angles disclosed for Form 1 and Form 2 of ceftolozane sulfate (as disclosed herein). Referring to DVS the isotherm plot in FIG. 5, the lower curve corresponds to ceftolozane sulfate in solid Form 2, and the upper curve is corresponds to ceftolozane sulfate in solid Form 1. The Y-axis of the DVS plot is change in mass. The X-axis of DVS plot refers to the percent relative humidity (RH) of the sample. Reference point 10 in FIG. 5 is the starting point of Form 2 in DVS experiment. The lower portion of the curve in FIG. 5 was obtained by measuring the change in mass of a ceftolozane sulfate sample in solid Form 2 while increasing relative humidity (RH) in the sample, starting at reference point 10 of the lower curve from reference point 10 (Form 2) and moving toward reference point 20 (Form 1). Based on the data collected, the ceftolozane sulfate in the sample converted from Form 2 to Form 1 when the sample was exposed to conditions between 50% RH (reference point 12) and 70% RH (reference point 15). Referring again to the lower curve in FIG. 5, ceftolozane sulfate in Form 1 is present in the sample from 70% RH to reference point 20, where the sample is ceftolozane sulfate is in crystalline Form 1. Referring to the upper curve in FIG. 5, from reference point 20 to reference point 30, the ceftolozane sulfate in the sample material remains as solid Form 1. From reference point 30 to around 20% RH (reference point 35 on the upper curve), the crystalline form of ceftolozane sulfate in the material transforms from Form 1 to Form 2. As the relative humidity of the sample was dropped below about 20% on the upper curve between reference point 30 and reference point 40 (0% RH), the ceftolozane sulfate became more amorphous, with some residual Form 2 remaining at reference point 40. In summary, the ceftolozane sulfate in the sample was present as Form 2 at reference point 10 (40% RH), converted from Form 2 to Form 1 between reference point 12 and reference point 15 on the lower curve, remained as solid Form 1 between reference point 20 and reference point 30 on the upper curve, converted from Form 1 to Form 2 between reference point 30 and reference point 35 on the upper curve, and remained as solid Form 2 from reference point 35 to reference point 40 (with formation of amorphous solid form in the sample). From reference point 40 to reference point 10 (lower curve), increasing the relative humidity of the partially crystalline Form 2 material resulted in material retaining some ceftolozane sulfate in Form 2 (partially crystalline).

Example 2d

Representative Example of Process to Manufacture Novel Solid Forms of Ceftolozane Sulfate Using the process of steps 1-9 (below), active ceftolozane sulfate Form 2 was obtained as a white solid, with a weight assay of 76.2% (determined using HPLC method described with respect to parameters in Table 9 herein) and purity of 98.7% AUC using HPLC (determined using HPLC method discussed with respect to Table 10 herein). The ceftolozane sulfate solid Form 1 was produced by steps 1-8 in the procedure below, and further dried (step 9) to obtain ceftolozane sulfate Form 2. The materials used in the process below are summarized in Table 8a.

TABLE 8a

| Step | Material | MW (g/mol) | Active (kg) | Amount (L) | Volume (L/kg) | Molar equiv. |
|---|---|---|---|---|---|---|
| 1 | Ceftolozane solution | 666.7 | 55 | 650 | N/A | 1 |
| 2 | 50% (w/w) sulfuric acid | 98.1 | 41 | 29 | N/A | 2.5 |
| 3 | Ceftolozane sulfate seed | 666.7 | 0.20 | N/A | N/A | N/A |
| 5 | Isopropyl alcohol (IPA) | 60.1 | N/A | 1653 | 30 | N/A |
| 8 | IPA/Water (4:1) | N/A | N/A | 221 | 4 | N/A |

1. Polish filter (1 micrometer) the ceftolozane solution (85 g/L, 650 L) into a glass lined reactor and adjust the temperature to 8-12 degrees C., with a target temperature of about 10 degrees C. This temperature is maintained through step 6.
2. Charge 50% (w/w) sulfuric acid (41 kg, 29 L, 2.5 equiv) to the solution in the reactor of step 1 over 10-30 minutes.
3. (optional, but preferred step) Charge ceftolozane sulfate seed (200 g, 0.3% by weight) to the reactor and stir the solution. (Note: nucleation was observed upon seeding)
4. Age the batch in the reactor for 3 hours.
5. Charge isopropanol (IPA) (1650 L, 30 volumes) to the reactor at a uniform rate of 4-5 vol/hr. (6-7 hours addition time, target of 6.5 hours) (Note: if the rate of IPA addition is not uniform, the purity levels of the product may be adversely affected)
6. Stir the batch in the reactor for 1-6 hours, target of 2 hours.
7. Filter the resulting ceftolozane sulfate slurry from the reactor.
8. Wash the ceftolozane slurry cake from step 7 with a solution of 4:1 IPA/water. (221 L, 4 volumes)
9. Dry the solid from step 8 under vacuum using a dry nitrogen purge, with a nitrogen temperature of 15-35 degrees C., target temperature of about 25 degrees C. The drying process should be monitored by measuring for residual water and IPA levels in the cake. The drying process can be completed when the residual water content is less than about 8.5% and IPA levels are less than about 5000 ppm. Typically, drying is complete within 48 hours.

Example 3

Comparative Ceftolozane Solvent Stability Test

This stability study was to evaluate stability and purity of ceftolozane sulfate in different solvent systems.

Sample 1 was a solvent system used to prepare crystalline ceftolozane sulfate from a mixture of isopropanol and water, as described in Example 2b (in the absence of ethanol). Sample 2 was solvent system used to obtain crystalline ceftolozane sulfate prepared according to the procedure of U.S. Pat. No. 7,129,232, wherein the crystals were precipitated from a mixture of ethanol and water.

Sample 1 and sample 2 were maintained for 6 days (as described in Example 2a, with continuous stirring). The purity of ceftolozane in the samples in each solvent system was measured by HPLC at day 0, day 3, and day 6.

Surprisingly, the purity of ceftolozane sulfate in sample 1 was significantly higher than the purity of ceftolozane sulfate in sample 2 (see Table 8b).

TABLE 8b

The purity of ceftolozane in ceftolozane sulfate in different solvent systems used to obtain different solid forms

| Sample | 0 | 3 days | 6 days |
|---|---|---|---|
| 1 | 96.74% | 87.39% | 81.94% |
| 2 | 96.84 % | 87.97% | 67.74% |

Example 4

Determination of Water Content for Crystalline Ceftolozane

Water content of crystalline ceftolozane sulfate (prepared according to Example 2a as Form 1) was determined using a Mettler Toledo Karl Fischer volumetric titrator V30 that was connected to a Mettler Toledo Stromboli oven sample changer. AquaStar CombiTitrant 5 (EMD; Cat. No. 1.88005.1045; Lot No. 51096) was used as the titrant and the AquaStar Combi-Methanol (EMD; Cat. No 1.88009.1045; Lot No 53046) was used as the solvent. For data processing, the LabX software version 3.1.1.0 was employed.

The Hydranal Water Standard for KF-Oven (Fluka; Cat. No. 34693; Lot No. SZBB010AV) that is expected to contain 5% water was weighed accurately in duplicate at or very close to 200 mg. The crystalline ceftolozane sulfate (15-18 mg) was weighed accurately in triplicate in separate 20 mL Stromboli sample vials. The vials were sealed with aluminum seals and rubber caps. A blank vial was prepared by sealing an empty 20-mL Stromboli vial with the aluminum seal and the rubber cap. The blank vial was used to determine the background moisture in air inside the vial. All the vials were loaded onto the Stromboli oven sample changer. Weights of the water standard and the ceftolozane sulfate wet cake samples were entered in grams into the titrator program sequence. The water standard and the blank vial were equilibrated at 150° C. The crystalline ceftolozane sulfate samples were equilibrated at 130° C. Nitrogen flow at 40-50 mL/min was used to transport the moisture through the transfer tube into the titator vessel. Mixing time of 180 s was used and the data acquisition was programmed with a maximum start drift of 15 µg/min. At the end of the runs, the titrator software provided the water content in percent by weight. The KF titrator passed the accuracy test as the mean of the duplicate readings for the water standard was between the acceptance range of 4.80-5.20%. Water content results for crystalline ceftolozane sulfate derived from the triplicate weighings were recorded and the mean was reported. The water content determination follows the equation as described below. The software described above provided the result directly after factoring in the background moisture content without any need for manual computation.

A sample of crystalline ceftolozane sulfate prepared according to Example 1 was found to contain about 26.3% by weight of water.

Example 5

Determining Concentration of Ceftolozane

Standards and samples are prepared in 50 mM sodium perchlorate monohydrate, pH 4.00. A quantitation standard (Standard Solution 1) and check standard (Standard Solution 2) are both prepared at the target working concentration of 0.3 mg/mL taking into consideration the potency, as-is of the standard. The samples are prepared at the target active concentration of 0.3 mg/mL by preparing a sample at 0.04% (w/v).

TABLE 9

HPLC Conditions for Concentration Determination

| | |
|---|---|
| Column | Develosil ODS-UG-5, 5 µm, 250 mm × 4.6 mm, or |
| Guard columns | Develosil ODS-UG-5, 5 µm, 10 mm × 4.0 mm, or |
| Column temperature | 40° C. ± 2° C. |
| Mode | Gradient |
| Mobile phase A | 50 mM Sodium perchlorate monohydrate, pH 2.50 |
| Mobile phase B | 90% Acetonitrile in water |

| Pump conditions | Time (min) | % A | % B |
|---|---|---|---|
| | 0.0 | 89.5$^a$ | 10.5$^a$ |
| | 10.0 | 89.5$^a$ | 10.5$^a$ |
| | 15.0 | 20 | 80 |
| | 20.0 | 20 | 80 |
| | 20.1 | 89.5$^a$ | 10.5$^a$ |
| | 25.0 | 89.5$^a$ | 10.5$^a$ |

| | |
|---|---|
| Flow rate | 1.0 mL/minute |
| Detection | UV at 254 nm |
| Auto-sampler temperature | 4° C. ± 2° C. |
| Injection volume | 10 µL |
| Run time | 25 minutes |

$^a$The ratio of Mobile phase A to Mobile phase B may be adjusted to achieve the desired retention time, however the isocratic ratio of % A to % B must be identical for both isocratic intervals.

Standard Solution 1 is injected 6 times at the beginning of the analysis to establish system suitability and precision.

System suitability is determined using the first injection of Standard Solution 1. The tailing factor for the ceftolozane peak be 0.8 to 1.5 and the retention time for the ceftolozane peak should be 10.0 minutes ±1.5 minutes. The binary pump setting at isocratic portions of the run (0.0 to 10.0 minutes and 20.1 to 25.0 minutes) may be adjusted to achieve the ceftolozane peak retention time.

Additional suitability of the run is determined by:
% RSD of 6 Standard Solution 1 injections must be less than 1.0% The Standard Solution 2 recovery must be 100.0±1.0%.

The retention time of Standard Solution 2 must be ±5% of the RT of the first injection of Standard solution 1.

The tailing factor of ceftolozane in Standard Solution 2 must be 0.8 to 1.5.

Each sample is prepared in duplicate and injected in singlet. The ratio of the response factor for the two preparations must be within 100.0±1.0%.

The mean ceftolozane potency, as is, is reported in µg/mg and calculated using the following equations:

$$\text{Potency, as-is } (\mu g/mg) = \frac{Ac \times Cstd \times 1000 \times Vc}{Astd \times Wc};$$

where:
Ac=Ceftolozane peak area in sample chromatogram;
Cstd=Ceftolozane Standard 1 concentration, mg/mL;
Astd=Average peak area in 6 injection of standard 1;
Wc=Sample weight, mg;
Vc=Sample volume, mL;
1000=Conversion from mg to µg; and $$\text{Mean Potency, as-is } (\mu g/mg) = \frac{(\text{Prepartation 1} + \text{Preparation 2})}{2}.$$

The mean ceftolozane assay, anhydrous and sulfuric acid free, is reported in % and calculated using the following equation:

Mean Assay(%)=Potency×10/(100−Water Content−Sulfuric Acid);

where:
Potency=Mean Potency, as-is, µg/mg;
Water Content=Mean water content, %; and
Sulfuric Acid=Mean sulfuric acid content, %.

Example 6

Determining Water Content of Ceftolozane

Testing for water content is performed using a Stromboli oven and volumetric titrator in triplicate using separate weighing of 180 mg of ceftolozane sulfate. The test sample is extracted at 130° C., moisture is transferred to the titration vessel and titrated to the potentiometric end point. The percent moisture is calculated based on the weight of the sample, and the average of the three values is reported.

Example 7

Determination of the Purity of Ceftolozane Sulfate

Ceftolozane sulfate samples are prepared at a concentration of 1 mg/mL in diluent (50 mM sodium perchlorate monohydrate, pH 4.00). The system suitability standard (SST) is prepared at a concentration of 1 mg/mL of ceftolozane sulfate containing specified impurities in diluent (50 mM sodium perchlorate monohydrate, pH 4.00). Ceftolozane samples and SST are stored in a refrigerated autosampler tray at 4±2° C. and the samples are only stable for 5 hours at this condition. The HPLC conditions are listed in Table 10.

TABLE 10

HPLC Conditions for HPLC-RT, Related Substances, and Purity Method

| | |
|---|---|
| Column | Develosil ODS-UG-5, 5 µm, 250 mm × 4.6 mm, or equivalent |
| Guard columns | Develosil ODS-UG-5, 5 µm, 10 mm × 4.0 mm, or equivalent |
| Column temperature | 45° C. ± 2° C. |
| Mode | Gradient |
| Mobile phase A | 50 mM Sodium perchlorate monohydrate, pH 2.50 |
| Mobile phase B | 63 mM Sodium perchlorate monohydrate, pH 2.50: ACN 80:20 |

| Pump conditions | Time (min) | % A | % B |
|---|---|---|---|
| | 0.0 | 97.5 | 2.5 |
| | 3.0 | 73.0[a] | 27.0[a] |
| | 33.0 | 68.0[a] | 32.0[a] |
| | 63.0 | 0.0 | 100 |
| | 88.0 | 0.0 | 100 |
| | 88.1 | 97.5 | 2.5 |
| | 105.0 | 97.5 | 2.5 |

| | |
|---|---|
| Flow rate | 1.0 mL/minute |
| Detection | UV at 254 nm |
| Auto-sampler temperature | 4° C. ± 2° C. |
| Injection volume | 10 µL |
| Run time | 105 minutes |

[a]The ratio of mobile phase A to mobile phase B from 3 to 33 minutes may be adjusted to achieve the desired retention times.

At the beginning of each run, the diluent blank and SST are each injected in singlet. The system suitability is determined using the SST. The tailing factor for the ceftolozane peak should be between 0.8 and 1.5, and the retention time for the ceftolozane peak should be 24.0 minutes ±1.0 minutes. The binary pump setting between 3.0 and 33.0 minutes may be adjusted to achieve the ceftolozane peak retention time.

Each sample is prepared in singlet and injected twice. Only impurities >LOD (0.008% Area) are integrated. The peak area percentage for each impurity >LOD is taken directly from the chromatogram. The mean % area of each peak is calculated and the absolute difference of any peak in the two replicates cannot be >0.030%. The purity and related substances are determined based on relative area % of each peak with respect to the total peak area of the sample. The total impurities are the sum of the individual impurities >LOD. The calculations are as follows:

$$\% \text{ Impurity (\% Area)} = \frac{\text{Area}_{impurity}}{\text{Area}_{Total}} \times 100\%;$$

where:
$\text{Area}_{Impurity}$=Area of the Individual Impurity Peak; and
$\text{Area}_{Total}$=Total Area of all peaks >LOD including Ceftolozane.

$$\text{Purity (\% Area)} = \frac{\text{Area}_{Ceftolozane}}{\text{Area}_{Total}} \times 100\%;$$

where:
$\text{Area}_{Ceftolozane}$=Area of the Ceftolozane Peak; and
$\text{Area}_{Total}$=Total Area of all peaks ≥LOD including Ceftolozane.

Total Impurities(% Area)=100−Purity(% Area).

Individual specified impurities equal to or above the limit of quantitation (LOQ) (0.027% Area) are reported. Individual unspecified impurities equal to or above 0.03% are also reported.

Example 8

Lyophilization of Ceftolozane Solid Forms

Sterile ceftolozane compositions suitable for combination with tazobactam to form a pharmaceutical composition are prepared as a lyophilized powder from the ceftolozane sulfate comprising solid Form 2 by compounding the drug substance with excipients into an aqueous solution, aseptically filtering the solution, lyophilizing the solution, then grinding, sieving and packaging the sterile lyophilized powder. The physical stability of the bulk solution at varying concentrations was examined and concentrations up to 150 mg ceftolozane free base/g solution were found suitable. All the registration batches were prepared using 150 mg/g ceftolozane concentration in the compounding solution and this concentration is proposed for commercial manufacturing. The resulting ceftolozane composition solubility was assessed in a concentration range proposed for manufacturing, in the presence of excipients intended for use in the ceftolozane formulation for use in the pharmaceutical composition. For each sample, the ratio of active to inactive ingredients was conserved. Samples were adjusted to pH 6.9, held at 2 to 8° C., and visually assessed for any precipitation. The results are reported in Table 11.

TABLE 11

Ceftolozane Precipitation Time as Function of Solution Concentration, 2 to 8° C.

| Ceftolozane Sulfate Concentration, mg/g | Ceftolozane Free Base Concentration, mg/g | Time to Precipitate |
|---|---|---|
| 200 | 174 | 2 hours |
| 189 | 165 | <18 hours |
| 178 | 156 | >24 hours[1] |
| 172 | 150 | >48 hours |
| 149 | 130 | >24 hours[a] |

[1]Last observation was made at 24 hour; no sign of precipitation was noticed

Based on these observations, ceftolozane bulk solution with up to 150 mg ceftolozane free base/g solution can be held at 2 to 8° C. for up to 48 hours without affecting its solubility. The suitability of compounding to 150 mg ceftolozane free base/g solution at 10±2.5° C. was confirmed during the manufacturing of batches on the laboratory, pilot and engineering scale. Refer to Table 12 for solution stability data. The purity data in Table 12 was generated using a modified version of the HPLC method that is described in Table 10. As part of the modification, the initial mobile phase composition comprised 75% mobile phase A and 25% mobile phase B. This composition was ramped to 70% mobile phase A and 30% mobile phase B in 30 minutes followed by a ramp to 100% mobile phase B over another 30 minutes. The 100% mobile phase B was then held constant for 25 minutes, after which the mobile phase composition was reverted back in 0.1 minutes to initial conditions of 75% mobile phase A and 25% mobile phase B. Column equilibration was performed at the initial mobile phase composition for up to 110 minutes, thereby giving a total HPLC run time of 110 minutes. The limit of quantification determined for the method with the conditions described above was 0.015% and therefore all individual specified impurities equal to or above 0.015% were reported.

A compounding temperature of 10±2.5° C. was targeted to maintain ceftolozane purity. To confirm the compounding solution stability, a study was conducted in which ceftolozane was prepared according to the proposed commercial process and held at 10±2.5° C. for up to 2 days. The solution was sampled and tested for ceftolozane potency and purity/impurities. The results are provided in Table 12. The data indicated ceftolozane impurity profile was essentially unchanged from initial and none of the individual related substances increases more than 0.10%. Therefore, a 24 hour maximum hold time is proposed for the commercial process.

TABLE 12

Effect of Hold Time on Purity/Impurity Profile of Ceftolozane Bulk Solution

| Time from Compounding | $t_0$ | 4 h | 18 h | 24 h | Day 2 |
|---|---|---|---|---|---|
| Total Purity, % | 98.7 | 98.8 | 98.6 | 98.6 | 98.7 |
| Total Impurities, % | 1.2 | 1.4 | 1.4 | 1.3 | 1.3 |

The ceftolozane bulk solution is rendered aseptic via sterilizing filtration. For routine commercial manufacturing, the compounded solution will be first filtered through a bioburden reduction filter, 0.45 μm, then sterile filtered through two 0.22 μm filters in sequence and the filter integrity of the 0.22 μm filters will be assessed during manufacturing.

Through a series of studies on both the pilot and commercial scale lyophilization equipment, the lyophilization process was developed and shown to be suitable: across a range of solution concentrations, at a variety of lyophilizer tray fill depths, following an array of lyophilization cycle parameters, in a number of lyophilizers, of both laboratory and commercial scale, and in two different commercial lyophilization suites.

In particular, six different lyophilizers (one pilot lyophilizer and five commercial lyophilizers from two separate commercial suites) have been used to make acceptable ceftolozane material using concentrations as high as 150 mg ceftolozane free base/g solution, fill depths from 1 to 3 cm, and different cycle parameters, including primary and/or secondary drying temperatures as high as 40° C. Based on these studies, freezing the product to at least −40 to −45° C. was considered an appropriate target. Primary drying temperatures are also typically set based on the glass transition temperature of the frozen bulk solution to minimize collapse. However, on occasion, the collapse may be prevented by using primary drying temperatures that are dictated by the full melt temperature, vs. the glass transition temperature. Therefore, studies were performed to examine these two temperatures more closely, to determine which would be controlling to prevent collapse. A variety of lyophilization conditions and instrumentation have been shown to be robust across a range of lyophilization conditions. Therefore, the preferred lyophilization cycles for producing lyophilized ceftolozane compositions from a solution comprising ceftolozane sulfate solid Form 2 have one or more of the following characteristics: (1) not more than 150 mg ceftolozane free base/g bulk solution concentration, (2) no more than 3 cm fill depth, (3) cycle parameters including: freezing to at least −40 to −45° C., (4) drying to no more than 40° C., (4) single- or multi-step drying and setting chamber pressure during the start of primary drying at not more than 400μ bar.

Example 9

Preferred Pharmaceutical Composition Comprising Ceftolozane and Tazobactam ("Representative Ceftolozane/Tazobactam Product")

Pharmaceutical compositions comprising ceftolozane and tazobactam can be obtained as described herein. A Representative Ceftolozane/Tazobactam Product is described in Table 14 below (ceftolozane and tazobactam for injection) as an injectable antibacterial combination product consisting of the cephalosporin antibacterial ceftolozane sulfate and the beta-lactamase inhibitor tazobactam sodium for intravenous administration.

TABLE 13

Excipients Used in Ceftolozane composition

| Component | Function | Amount, mg/Vial | Concentration in Infusion Solution, % | Rationale for Inclusion | Inactive Ingredients Database (IID) Range |
|---|---|---|---|---|---|
| Citric acid | Chelating agent | 21 | 0.02 | Used to prevent discoloration and degradation | 0.0025 to 50% |
| Sodium Chloride | Stabilizing agent | 487 | 0.49 | Used as a stabilizing agent for ceftolozane sulfate | 0.187 to 45% |
| L-arginine | Alkalizing agent | 600[i] Q.S. for pH adjustment | 0.60 | Used to adjust ceftolozane solution pH | 0.29 to 88% |

[i]L-arginine is added as needed to achieve pH 6.5 ± 0.5; 600 mg per vial is considered a representative total amount.

TABLE 14

Unit Compositions of Ceftolozane/Tazobactam for Injection, 1000 mg/500 mg

| Component | | Function | Nominal Composition mg per Vial |
|---|---|---|---|
| Ceftolozane composition[1] | Ceftolozane Sulfate (Solid Form 2) | Active | 1147 |
| | Citric Acid, Anhydrous | Chelating Agent | 21 |
| | Sodium Chloride | Stabilizing Agent | 487 |

TABLE 14-continued

Unit Compositions of Ceftolozane/Tazobactam for Injection, 1000 mg/500 mg

| Component | Function | Nominal Composition mg per Vial |
|---|---|---|
| L-Arginine | Alkalizing Agent | 600[2] |
| | | Q.S. for pH adjustment |
| Tazobactam Sodium[3] | Active | 537 |
| Nitrogen | Processing Aid[4] | Q.S. |
| | Total Weight | 2792 |

1) Actual amount of ceftolozane composition will vary based on the measured potency. Ceftolozane sulfate, 1147 mg, corresponds to 1000 mg ceftolozane free base.
2) L-arginine is added as needed to achieve pH 6.5 ± 0.5; 600 mg per vial is considered a representative total amount.
3) Actual weight of tazobactam sodium will vary based on the measured potency. Tazobactam sodium 537 mg, corresponds to 500 mg tazobactam free acid
4) Nitrogen blanket is applied after powders are dispensed to the vial and prior to insertion of stopper.

A first aqueous solution comprising ceftolozane sulfate Form 2 and the ingredients in the ceftolozane composition in Table 13 is lyophilized in the absence of tazobactam to provide the lyophilized ceftolozane composition. The first aqueous solution comprises ceftolozane sulfate and the specific excipients in the preferred compositions, in an amount per unit dosage form provided by the quantities and functions as provided in Table 14. All excipients are compendial and typical for sterile pharmaceutical dosage forms, requiring no additional treatment prior to use in the formulation. The excipients are used in levels within the range established in other FDA approved products as described in the Inactive Ingredients Database (IID). A second solution comprising tazobactam acid and sodium bicarbonate is lyophilized in the absence of ceftolozane to obtain the Tazobactam Sodium Composition in Table 14. Subsequently, the lyophilized Tazobactam Sodium Composition is dry blended with the lyophilized Ceftolozane composition comprising tazobactam sodium and ceftolozane sulfate in a weight ratio providing 500 mg of tazobactam acid equivalent per 1,000 mg of ceftolozane active equivalent.

Example 10

Reconstitution of Ceftolozane/Tazobactam Preparation Prior To Administration to a Subject The ceftolozane/tazobactam composition of Example 9 was reconstituted prior to intravenous (IV) administration. In accordance with one embodiment of the method of treatment, immediately prior to injection into a patient, a single vial, containing 1500 mg ceftolozane and tazobactam, was reconstituted with 20 mL 0.9% NaCl (normal saline) and diluted into a 80 mL bag of sterile water for injection for a total volume of 100 mL.

The ceftolozane and tazobactam composition was reconstituted in accordance with the procedure as follows:

Obtain 1 vial of ceftolozane/tazobactam unit dosage form, 1500 mg/vial. Record the site and subject number and time and date of preparation in the spaces provided on the vial label. Ceftolozane/tazobactam of Example 9 does not contain a bacteriostatic preservative. Aseptic technique must be followed in preparing the infusion solution.

Aseptically reconstitute a lyophilized vial of ceftolozane/tazobactam unit dosage form, 1500 mg with 10 ml water for injection or 0.9% Sodium Chloride for injection, USP (normal saline) and gently shake to dissolve. The final volume is approximately 11.4 mL. The resultant concentration is approximately 132 mg/mL.

Using aseptic technique, withdraw the entire contents (approximately 11.4 mL) of the reconstituted vial using a syringe and add it to an infusion bag containing 100 mL of 0.9% Sodium Chloride for Injection, USP (normal saline) or 5% Dextrose Injection, USP. Ensure the entire volume of the reconstituted vial is added to the infusion bag.

Gently swirl the contents of the IV bag to ensure complete mixing and dissolution of the drug. The final volume of diluted ceftolozane/tazobactam unit dosage form of Example 9 for infusion will be ~111 ml. The entire contents of the infusion bag of ceftolozane/tazobactam is administered to each subject. This means that the infusion line is flushed with sterile saline to completely administer the proper dose).

Inspect the infusion bag for excess air, visible contamination and leaks. The diluted solution should be clear.

Upon constitution with sterile water for injection or 0.9% sodium chloride (normal saline) injection, the ceftolozane/tazobactam solution in the vial may be held for 1-hour prior to transfer and dilution in the infusion bag.

Following dilution of the solution with normal saline or 5% dextrose, the ceftolozane/tazobactam solution obtained from the ceftolozane/tazobactam composition of Example 9 is stable for 24 hours when stored at room temperature or 10 days when stored under refrigeration at 2 to 8° C. (36 to 46° F.).

Example 11

Melting Point of Ceftolozane Sulfate Form 2

Melting point experiment was performed for ceftolozane sulfate form 2 using the SRS Optimelt melting point apparatus. SRS-certified vanillin and phenacetin were used to verify the system performance. The temperature scan from 100° C. to 400° C. was performed for ceftolozane sulfate. The material decomposed prior to melting. The decomposition, as indicated by the distinct change in color, appeared to commence at about 170° C.

Example 12

TGA and DSC of Ceftolozane Sulfate Form 2

Figure 3:
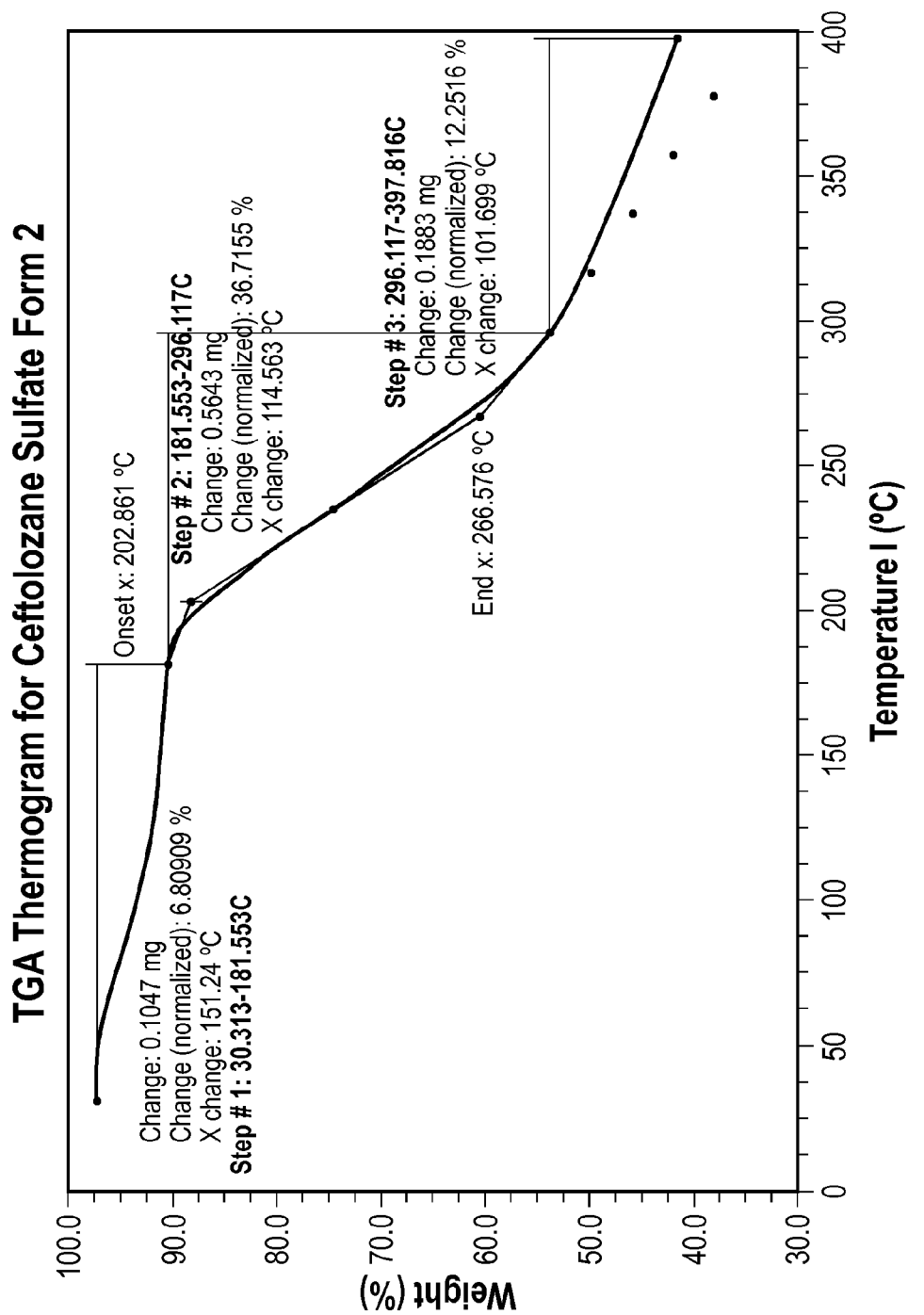
FIG. 3 is a thermogravimetric analysis (TGA) curve for ceftolozane sulfate in a solid form designated herein as Form 2.
Figure 4:
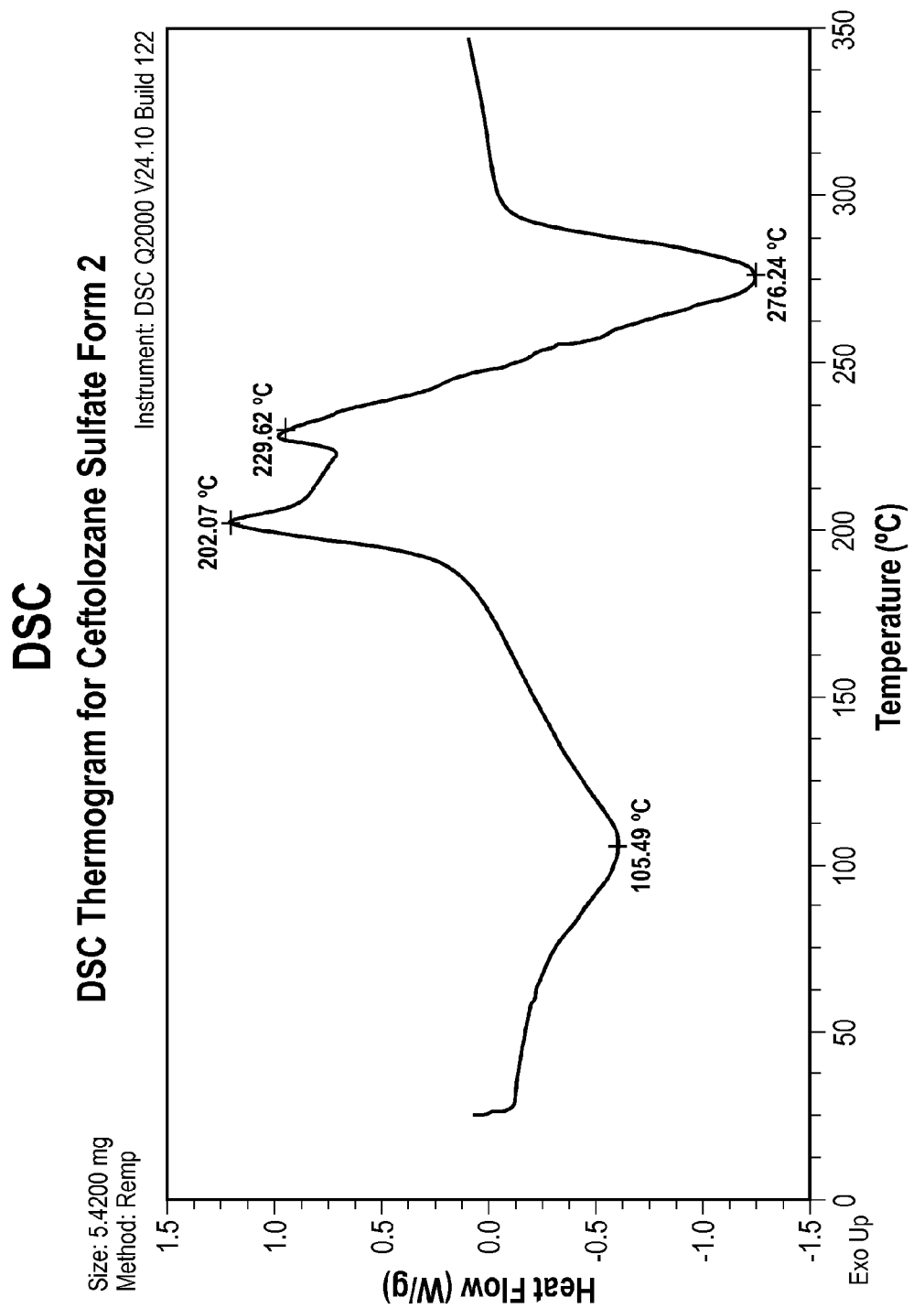
FIG. 4 is a differential scanning calorimetry (DSC) thermograms for ceftolozane sulfate in a solid form designated herein as Form 2.

Thermogravimetric analysis (TGA) and differential scanning calorimetry (DSC) thermograms are shown in FIG. 3 and FIG. 4, respectively. An initial weight loss of 6.8% observed in the TGA thermogram from initial temperature to 181° C. is consistent with the content of water and residual isopropanol present in ceftolozane sulfate, lot 440637 0004 2. Analysis of the thermogram beyond 181° C. indicated that ceftolozane sulfate likely undergoes degradation beyond this temperature. The DSC thermogram exhibited a broad endotherm with the minima at about 105.49° C. The subsequent exotherm in the thermogram is indicative of decompostion that is consistent with the observation in the melting point experiment.

Example 13

Hygroscopicity of Ceftolozane Sulfate Form 2

Hygroscopicity of ceftolozane sulfate, Form 2 was assessed using the SMS DVS Intrinsic moisture sorption analyzer equipped with a calibrated Rotronic probe. The temperature was maintained at 25° C. and the material was exposed to relative humidity from 0 to 90%. Ceftolozane sulfate showed continuous adsorption of water through the cycle with total uptake of 23% at 90% relative humidity indicating that ceftolozane sulfate is hygroscopic.

What is claimed:

1. Solid Form 2 of ceftolozane sulfate that produces an X-ray powder diffraction (XRPD) pattern having diffractions at angles (2 theta±0.2) of 4.4, 8.8. 11.0, 14.9, and 17.7.

2. The solid form of ceftolozane sulfate of claim 1 that produces Raman shift peaks (±5 cm$^{-1}$) at about 151 cm$^{-1}$, 684 cm$^{-1}$, and 802 cm$^{-1}$.

3. The solid form of ceftolozane sulfate of claim 1 characterized by a differential scanning calorimetry (DSC) endotherm having a minima at about 105 degrees C.

4. The solid form of ceftolozane sulfate of claim 1, characterized by a thermogravimetric analysis (TGA) with a weight loss of about 6.8% between 25-181 degrees C.

5. The solid form of ceftolozane sulfate of claim 1, characterized by
   a. a differential scanning calorimetry (DSC) endotherm having a minima at about 105 degrees C.;
   b. a thermogravimetric analysis (TGA) with a weight loss of about 6.8% between 25-181 degrees C.; and
   c. Raman shift peaks (±5 cm$^{-1}$) at 151 cm$^{-1}$, 684 cm$^{-1}$, 802 cm$^{-1}$, 1174 cm$^{-1}$, and 2953 cm$^{-1}$.

6. A pharmaceutical composition comprising the solid form of ceftolozane sulfate designated as ceftolozane sulfate Form 2 that produces an X-ray powder diffraction (XRPD) pattern having diffractions at angles (2 theta±0.2) of 4.4, 8.8. 11.0, 14.9, and 17.7.

7. The pharmaceutical composition of claim 6, wherein the ceftolozane sulfate produces Raman shift peaks (±5 cm$^{-1}$) at about 151 cm$^{-1}$, 684 cm$^{-1}$, 802 cm$^{-1}$, 1174 cm$^{-1}$, and 2953 cm$^{-1}$.

8. The pharmaceutical composition of claim 7, further comprising ceftolozane sulfate in a solid form that produces an X-ray powder diffraction (XRPD) pattern having diffractions at angles (2 theta±0.2) of 12.4, 16.4, 22.6, 25.1 and 28.0.

9. The pharmaceutical composition of claim 6, further comprising tazobactam.

10. The pharmaceutical composition of claim 6, further comprising a pharmaceutically acceptable excipient.

11. The pharmaceutical composition of claim 10, wherein the pharmaceutically acceptable excipient is selected from the group consisting of: sodium chloride, L-arginine, citric acid and mixtures thereof.

12. The pharmaceutical composition of claim 11, characterized by one or more of the following:
   a. a differential scanning calorimetry (DSC) endotherm having a minima at about 105 degrees C.;
   b. a thermogravimetric analysis (TGA) with a weight loss of about 6.8% between 25-181 degrees C.; and
   c. Raman shift peaks (±5 cm$^{-1}$) at 151 cm$^{-1}$, 684 cm$^{-1}$, 802 cm$^{-1}$, 1174 cm$^{-1}$, and 2953 cm$^{-1}$.

13. A pharmaceutical composition comprising a lyophilized ceftolozane composition obtained by a process comprising the steps of:
   a. combining the ceftolozane sulfate in a solid form designated as ceftolozane sulfate Form 2 that produces an X-ray powder diffraction (XRPD) pattern having diffractions at angles (2 theta±0.2) of 4.4, 8.8, 11.0, 14.9, and 17.7, with water, sodium chloride and L-arginine to form an aqueous solution; and
   b. lyophilizing the aqueous solution to form the lyophilized ceftolozane composition comprising ceftolozane sulfate.

14. The pharmaceutical composition of claim 13, wherein the lyophilization cycle is characterized by one or more of the following characteristics:
   a. not more than 150 mg ceftolozane free base/g bulk solution concentration,
   b. no more than 3 cm fill depth,
   c. freezing to at least −40° C. during the lyophilization cycle,
   d. drying to no more than 40° C., and
   e. single- or multi-step drying and setting chamber pressure during the start of primary drying at not more than 400µ bar.

15. The pharmaceutical composition of claim 13, further comprising tazobactam.

16. The pharmaceutical composition of claim 15, obtained by a process further comprising combining the lyophilized ceftolozane composition with tazobactam in a fixed dose combination providing about 500 mg of tazobactam active per 1,000 mg of ceftolozane active in the pharmaceutical composition.

17. A pharmaceutical composition comprising a lyophilized ceftolozane composition obtained by a process comprising the steps of:
   a. combining the ceftolozane sulfate of solid Form 2 that produces an X-ray powder diffraction (XRPD) pattern having diffractions at angles (2 theta±0.2) of 4.4, 8.8. 11.0, 14.9, and 17.7 with water to form an aqueous solution; and
   b. lyophilizing the aqueous solution to form the lyophilized ceftolozane composition comprising ceftolozane sulfate.

18. The pharmaceutical composition of claim 17, wherein the aqueous solution in step (b) further comprises tazobactam or a pharmaceutically acceptable salt thereof.

19. The pharmaceutical composition of claim 18, wherein the pharmaceutical composition comprises tazobactam sodium.

20. The pharmaceutical composition of claim 17, wherein the aqueous solution in step (b) is lyophilized in the absence of tazobactam.

21. The pharmaceutical composition of claim 17, wherein the pharmaceutical composition comprises the ceftolozane sulfate in an amount providing about 1,000 mg of ceftolozane active.

22. The pharmaceutical composition of claim 21, wherein the pharmaceutical composition further comprises about 500 mg of tazobactam active.

23. The pharmaceutical composition of claim 17, wherein the pharmaceutical composition comprises ceftolozane active and tazobactam active, and the ceftolozane sulfate is present in the pharmaceutical composition in an amount providing 1,000 mg of ceftolozane active per 500 mg of tazobactam active.

24. The pharmaceutical composition of claim 17, wherein the pharmaceutical composition comprises ceftolozane and a beta-lactamase inhibitor compound.

25. The pharmaceutical composition of claim 17, wherein the pharmaceutical composition comprises about 1,000 mg of ceftolozane active and 500 mg of tazobactam active.

26. The pharmaceutical composition of claim 17, obtained by a process further comprising combining the lyophilized ceftolozane composition with tazobactam in a fixed dose combination providing about 500 mg of tazobactam active per 1,000 mg of ceftolozane active in the pharmaceutical composition.

27. The pharmaceutical composition of claim 26, wherein the pharmaceutical composition comprises tazobactam sodium.

28. The pharmaceutical composition of claim 26, wherein the pharmaceutical composition comprises crystalline tazobactam.

29. The pharmaceutical composition of claim 26, wherein the aqueous solution is lyophilized in step (b) with a lyophilization cycle characterized by one or more of the following characteristics:
   a. not more than 150 mg ceftolozane free base/g bulk solution concentration,
   b. no more than 3 cm fill depth,
   c. freezing to at least −40° C. during the lyophilization cycle,
   d. drying to no more than 40° C., and
   e. single- or multi-step drying and setting chamber pressure during the start of primary drying at not more than 400μ bar.

30. The pharmaceutical composition of claim 26, characterized by one or more of the following:
   a. a differential scanning calorimetry (DSC) endotherm having a minimia at about 105 degrees C.;
   b. a thermogravimetric analysis (TGA) with a weight loss of about 6.8% between 25-181 degrees C.; and
   c. Raman shift peaks (±5 cm$^{-1}$) at 151 cm$^{-1}$, 684 cm$^{-1}$, 802 cm$^{-1}$, 1174 cm$^{-1}$, and 2953 cm$^{-1}$.

\* \* \* \* \*